United States Patent
Horst et al.

(10) Patent No.: US 12,017,017 B2
(45) Date of Patent: *Jun. 25, 2024

(54) CATHETER INSERTION DEVICE

(71) Applicant: TELEFLEX MEDICAL INCORPORATED, Morrisville, NC (US)

(72) Inventors: Benjamin Horst, Lititz, PA (US); Mark Spinka, Jenkintown, PA (US); Jacob Ammarell, Leesport, PA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 865 days.

This patent is subject to a terminal disclaimer.

(21) Appl. No.: 16/988,013

(22) Filed: Aug. 7, 2020

(65) Prior Publication Data

US 2020/0360665 A1 Nov. 19, 2020

Related U.S. Application Data

(63) Continuation of application No. 15/950,507, filed on Apr. 11, 2018, now Pat. No. 10,737,063.
(Continued)

(51) Int. Cl.
*A61M 25/00* (2006.01)
*A61M 25/01* (2006.01)
(Continued)

(52) U.S. Cl.
CPC .... *A61M 25/0136* (2013.01); *A61M 25/0097* (2013.01); *A61M 25/0113* (2013.01);
(Continued)

(58) Field of Classification Search
CPC .......... A61M 25/0136; A61M 25/0097; A61M 25/0113; A61M 25/0606; A61M 25/0618;
(Continued)

(56) References Cited

U.S. PATENT DOCUMENTS

| 4,160,383 A | 7/1979 | Rauschenberger |
| 4,311,137 A | 1/1982 | Gerard |

(Continued)

FOREIGN PATENT DOCUMENTS

| AU | 650317 B2 | 6/1994 |
| CN | 1178707 A | 4/1998 |

(Continued)

OTHER PUBLICATIONS

International Search Report and Written Opinion issued in PCT/US2018/027078, dated Jun. 29, 2018.

*Primary Examiner* — Robert J Utama
*Assistant Examiner* — Hamza A Darb
(74) *Attorney, Agent, or Firm* — BakerHostetler

(57) ABSTRACT

A catheter insertion device that allows for single-handed insertion of the catheter within the vasculature of the patient is disclosed. The catheter insertion device includes a handle, a needle cannula partially within the handle, a guidewire partially within the handle and the needle cannula, and a first actuator connected to the handle and the guidewire. The guidewire is movable relative to the handle in a distal direction away from the handle, and in a proximal direction towards the handle. A catheter assembly is removably coupled to the handle and is configured to slide on the needle cannula. A catheter hub may be connected to a proximal end of the catheter, and a catheter advancer base may be releasably connected to the catheter hub. The catheter insertion device may also include a needle support pivotally connected to the handle for supporting the needle cannula on a cantilever portion thereof.

20 Claims, 27 Drawing Sheets

Related U.S. Application Data

(60) Provisional application No. 62/485,167, filed on Apr. 13, 2017.

(51) Int. Cl.
*A61M 25/06* (2006.01)
*A61M 25/09* (2006.01)

(52) U.S. Cl.
CPC .... *A61M 25/0606* (2013.01); *A61M 25/0618* (2013.01); *A61M 25/09041* (2013.01)

(58) Field of Classification Search
CPC ........ A61M 25/09041; A61M 25/0102; A61M 25/0612; A61M 25/065; A61M 2210/12
See application file for complete search history.

(56) References Cited

U.S. PATENT DOCUMENTS

| | | |
|---|---|---|
| 4,616,648 A | 10/1986 | Simpson |
| 4,798,594 A | 1/1989 | Hillstead |
| 4,809,679 A | 3/1989 | Shimonaka et al. |
| 4,857,062 A | 8/1989 | Russell |
| 4,858,810 A | 8/1989 | Intlekofer et al. |
| 4,895,346 A | 1/1990 | Steigerwald |
| 4,895,565 A | 1/1990 | Hillstead |
| 4,929,241 A | 5/1990 | Kulli |
| 4,977,897 A | 12/1990 | Hurwitz |
| 5,007,901 A | 4/1991 | Shields |
| 5,009,391 A | 4/1991 | Steigerwald |
| 5,048,530 A | 9/1991 | Hurwitz |
| 5,053,017 A | 10/1991 | Chamuel |
| 5,057,084 A | 10/1991 | Ensminger et al. |
| 5,084,023 A | 1/1992 | Lemieux |
| 5,102,394 A | 4/1992 | Lasaitis et al. |
| 5,112,311 A | 5/1992 | Utterberg et al. |
| 5,116,323 A | 5/1992 | Kreuzer et al. |
| 5,135,504 A | 8/1992 | McLees |
| 5,176,647 A | 1/1993 | Knoepfler |
| 5,176,650 A | 1/1993 | Haining |
| 5,186,712 A | 2/1993 | Kelso et al. |
| 5,279,588 A | 1/1994 | Nicoletti et al. |
| 5,304,156 A | 4/1994 | Sylvanowicz et al. |
| 5,312,359 A | 5/1994 | Wallace |
| 5,318,541 A | 6/1994 | Viera et al. |
| 5,325,746 A | 7/1994 | Anderson |
| 5,330,438 A | 7/1994 | Gollobin et al. |
| 5,350,363 A | 9/1994 | Goode et al. |
| 5,366,441 A | 11/1994 | Crawford |
| 5,389,100 A | 2/1995 | Bacich et al. |
| 5,405,323 A | 4/1995 | Rogers et al. |
| 5,409,459 A | 4/1995 | Gambale |
| 5,409,464 A | 4/1995 | Villalobos |
| 5,458,613 A | 10/1995 | Gharibadeh et al. |
| 5,512,052 A | 4/1996 | Jesch |
| 5,527,290 A | 6/1996 | Zadini et al. |
| 5,562,619 A | 10/1996 | Mirarchi et al. |
| 5,562,631 A | 10/1996 | Bogert |
| 5,569,217 A | 10/1996 | Luther |
| 5,573,510 A | 11/1996 | Isaacson |
| 5,611,792 A | 3/1997 | Gustafsson |
| 5,613,663 A | 3/1997 | Schmidt et al. |
| 5,637,096 A | 6/1997 | Yoon |
| 5,676,658 A | 10/1997 | Erskine |
| 5,704,914 A | 1/1998 | Stocking et al. |
| 5,738,660 A | 4/1998 | Luther |
| 5,766,135 A | 6/1998 | Terwilliger |
| 5,769,795 A | 6/1998 | Terwilliger |
| 5,795,339 A | 8/1998 | Erskine |
| 5,827,239 A | 10/1998 | Dillon et al. |
| 5,858,007 A | 1/1999 | Fagan et al. |
| 5,879,331 A | 3/1999 | Osterlind |
| 5,974,438 A | 10/1999 | Neufeld |
| 6,050,976 A | 4/2000 | Thorne et al. |
| 6,053,870 A | 4/2000 | Fulton, III |
| 6,056,726 A | 5/2000 | Isaacson |
| 6,077,244 A | 6/2000 | Botich et al. |
| 6,117,108 A | 9/2000 | Woehr et al. |
| 6,197,001 B1 | 3/2001 | Wilson et al. |
| 6,213,978 B1 | 4/2001 | Voyten |
| 6,228,060 B1 | 5/2001 | Howell |
| 6,287,278 B1 | 9/2001 | Woehr et al. |
| 6,287,280 B1 | 9/2001 | Lampropoulos et al. |
| 6,299,602 B1 | 10/2001 | Miller et al. |
| 6,413,250 B1 | 7/2002 | Smith |
| 6,443,929 B1 | 9/2002 | Kuracina et al. |
| 6,461,362 B1 | 10/2002 | Halseth et al. |
| 6,506,181 B2 | 1/2003 | Meng et al. |
| 6,544,239 B2 | 4/2003 | Kinsey et al. |
| 6,547,762 B1 | 4/2003 | Botich et al. |
| 6,551,282 B1 | 4/2003 | Exline et al. |
| 6,565,542 B2 | 5/2003 | Kumar et al. |
| 6,582,402 B1 | 6/2003 | Erskine |
| 6,595,955 B2 | 7/2003 | Ferguson et al. |
| 6,602,240 B2 | 8/2003 | Hermann et al. |
| 6,610,016 B1 | 8/2003 | Violante et al. |
| 6,616,630 B1 | 9/2003 | Woehr et al. |
| 6,620,136 B1 | 9/2003 | Pressly, Sr. et al. |
| 6,626,869 B1 | 9/2003 | Bint |
| 6,629,959 B2 | 10/2003 | Kuracina et al. |
| 6,638,252 B2 | 10/2003 | Moulton et al. |
| 6,652,486 B2 | 11/2003 | Bialecki et al. |
| 6,652,490 B2 | 11/2003 | Howell |
| 6,685,721 B1 | 2/2004 | Kramer |
| 6,699,221 B2 | 3/2004 | Vaillancourt |
| 6,709,419 B2 | 3/2004 | Woehr |
| 6,719,726 B2 | 4/2004 | Meng et al. |
| 6,749,588 B1 | 6/2004 | Howell et al. |
| 6,796,962 B2 | 9/2004 | Ferguson et al. |
| 6,824,527 B2 | 11/2004 | Gollobin |
| 6,860,856 B2 | 3/2005 | Ward et al. |
| 6,860,865 B1 | 3/2005 | Feldgiebel |
| 6,902,546 B2 | 6/2005 | Ferguson |
| 6,953,448 B2 | 10/2005 | Moulton et al. |
| 6,972,002 B2 | 12/2005 | Thorne |
| 6,984,213 B2 | 1/2006 | Horner et al. |
| 6,986,749 B2 | 1/2006 | Wollschlager |
| 7,004,927 B2 | 2/2006 | Ferguson et al. |
| 7,008,402 B2 | 3/2006 | Ferguson et al. |
| 7,008,404 B2 | 3/2006 | Nakajima |
| 7,044,936 B2 | 5/2006 | Harding et al. |
| 7,125,396 B2 | 10/2006 | Leinsing et al. |
| 7,179,244 B2 | 2/2007 | Smith et al. |
| 7,186,239 B2 | 3/2007 | Woehr |
| 7,226,434 B2 | 6/2007 | Carlyon et al. |
| 7,247,148 B2 | 7/2007 | Murashita |
| 7,264,613 B2 | 9/2007 | Woehr et al. |
| 7,291,128 B2 | 11/2007 | Rossi et al. |
| 7,291,130 B2 | 11/2007 | McGurk |
| 7,341,573 B2 | 3/2008 | Ferguson et al. |
| 7,344,516 B2 | 3/2008 | Erskine |
| 7,347,838 B2 | 3/2008 | Kulli |
| 7,357,784 B2 | 4/2008 | Ferguson |
| 7,374,554 B2 | 5/2008 | Menzi et al. |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,476,244 B2 | 1/2009 | Buzzard et al. |
| 7,534,227 B2 | 5/2009 | Kulli |
| 7,544,184 B2 | 6/2009 | Cope et al. |
| 7,556,617 B2 | 7/2009 | Voorhees, Jr. et al. |
| 7,597,681 B2 | 10/2009 | Sutton et al. |
| 7,604,616 B2 | 10/2009 | Thoresen et al. |
| 7,608,057 B2 | 10/2009 | Woehr et al. |
| 7,611,485 B2 | 11/2009 | Ferguson |
| 7,611,499 B2 | 11/2009 | Woehr et al. |
| 7,618,395 B2 | 11/2009 | Ferguson |
| 7,625,360 B2 | 12/2009 | Woehr et al. |
| 7,632,243 B2 | 12/2009 | Bialecki et al. |
| 7,635,352 B2 | 12/2009 | Adams |
| 7,637,893 B2 | 12/2009 | Christensen et al. |
| 7,645,263 B2 | 1/2010 | Angel et al. |
| 7,651,476 B2 | 1/2010 | Kohler |
| 7,670,317 B2 | 3/2010 | Cindrich et al. |

(56) References Cited

U.S. PATENT DOCUMENTS

| | | |
|---|---|---|
| 7,682,331 B2 | 3/2010 | Carrez et al. |
| 7,682,344 B2 | 3/2010 | Barrelle |
| 7,691,088 B2 | 4/2010 | Howell |
| 7,713,243 B2 | 5/2010 | Hillman |
| 7,731,687 B2 | 6/2010 | Menzi et al. |
| 7,736,332 B2 | 6/2010 | Carlyon et al. |
| 7,736,337 B2 | 6/2010 | Carlyon et al. |
| 7,736,339 B2 | 6/2010 | Harding et al. |
| 7,736,340 B2 | 6/2010 | Harding et al. |
| 7,744,568 B2 | 6/2010 | Douglas et al. |
| 7,753,877 B2 | 7/2010 | Bialecki et al. |
| 7,762,993 B2 | 7/2010 | Perez |
| 7,806,849 B2 | 10/2010 | Woehr |
| 7,828,774 B2 | 11/2010 | Harding et al. |
| 7,833,199 B2 | 11/2010 | Franer et al. |
| 7,938,805 B2 | 5/2011 | Harding et al. |
| 7,951,121 B2 | 5/2011 | Weaver et al. |
| 7,967,829 B2 | 6/2011 | Gunderson et al. |
| 7,972,313 B2 | 7/2011 | Woehr et al. |
| 7,976,502 B2 | 7/2011 | Baid |
| 7,988,664 B2 | 8/2011 | Fiser et al. |
| 8,038,647 B2 | 10/2011 | Harding et al. |
| 8,048,039 B2 | 11/2011 | Carlyon et al. |
| 8,052,647 B2 | 11/2011 | Raulerson et al. |
| 8,066,675 B2 | 11/2011 | Cindrich et al. |
| 8,162,881 B2 | 4/2012 | Lilley, Jr. et al. |
| 8,162,939 B2 | 4/2012 | Shizuka |
| 8,177,772 B2 | 5/2012 | Christensen et al. |
| 8,211,070 B2 | 7/2012 | Woehr et al. |
| 8,216,188 B2 | 7/2012 | Millerd et al. |
| 8,235,971 B2 | 8/2012 | Christensen et al. |
| 8,251,950 B2 | 8/2012 | Albert et al. |
| 8,257,315 B2 | 9/2012 | Franer et al. |
| 8,273,056 B2 | 9/2012 | Kuracina et al. |
| 8,292,852 B2 | 10/2012 | Mulholland et al. |
| 8,298,181 B2 | 10/2012 | Perez |
| 8,328,762 B2 | 12/2012 | Woehr et al. |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,348,893 B2 | 1/2013 | Carlyon |
| 8,369,935 B2 | 2/2013 | Ryan |
| 8,382,721 B2 | 2/2013 | Woehr et al. |
| 8,403,886 B2 | 3/2013 | Bialecki et al. |
| 8,449,530 B2 | 5/2013 | Bacher et al. |
| 8,460,247 B2 | 6/2013 | Woehr et al. |
| 8,480,627 B2 | 7/2013 | Christiansen |
| 8,486,024 B2 | 7/2013 | Steube |
| 8,500,696 B2 | 8/2013 | Kobayashi et al. |
| 8,506,528 B2 | 8/2013 | Fiser et al. |
| 8,523,819 B2 | 9/2013 | Abe et al. |
| 8,535,271 B2 | 9/2013 | Fuchs et al. |
| 8,540,728 B2 | 9/2013 | Woehr et al. |
| 8,647,301 B2 | 2/2014 | Bialecki et al. |
| 8,715,250 B2 | 5/2014 | Tremblay |
| 8,721,546 B2 | 5/2014 | Belson |
| 8,886,292 B2 | 11/2014 | Chesbrough et al. |
| 8,926,563 B2 | 1/2015 | Steube |
| 8,932,258 B2 | 1/2015 | Blanchard et al. |
| 8,986,227 B2 | 3/2015 | Belson |
| 9,011,351 B2 | 4/2015 | Hoshinouchi |
| 9,126,017 B2 | 9/2015 | Albert et al. |
| 9,707,042 B2 | 7/2017 | Chesbrough et al. |
| 9,717,886 B2 | 8/2017 | Kuehn et al. |
| 9,872,971 B2 | 1/2018 | Blanchard |
| 9,950,139 B2 | 4/2018 | Blanchard et al. |
| 10,232,146 B2 | 3/2019 | Braithwaite et al. |
| 10,335,578 B2 | 7/2019 | Ishida |
| 10,357,636 B2 | 7/2019 | Sonderegger et al. |
| 10,384,039 B2 | 8/2019 | Ribelin et al. |
| 10,737,063 B2 * | 8/2020 | Horst ............... A61M 25/0136 |
| 2002/0004650 A1 | 1/2002 | Kuracina et al. |
| 2002/0026151 A1 | 2/2002 | Miller et al. |
| 2002/0177812 A1 | 11/2002 | Moulton et al. |
| 2003/0083620 A1 | 5/2003 | Luther et al. |
| 2004/0019329 A1 | 1/2004 | Erskine |
| 2004/0106891 A1 | 6/2004 | Langan et al. |
| 2004/0122373 A1 | 6/2004 | Botich et al. |
| 2004/0127855 A1 | 7/2004 | Core |
| 2005/0075606 A1 | 4/2005 | Botich et al. |
| 2005/0075609 A1 | 4/2005 | Latona |
| 2005/0096592 A1 | 5/2005 | Carlyon et al. |
| 2005/0256505 A1 | 11/2005 | Long et al. |
| 2005/0273057 A1 | 12/2005 | Popov |
| 2006/0025721 A1 | 2/2006 | Duffy et al. |
| 2006/0084964 A1 | 4/2006 | Knudson et al. |
| 2006/0167405 A1 | 7/2006 | King et al. |
| 2006/0229563 A1 | 10/2006 | O'Reagan et al. |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038187 A1 | 2/2007 | Albert et al. |
| 2007/0043422 A1 | 2/2007 | Shmulewitz et al. |
| 2007/0073221 A1 | 3/2007 | Bialecki et al. |
| 2007/0073270 A1 | 3/2007 | Christensen et al. |
| 2007/0123803 A1 | 5/2007 | Fujiwara et al. |
| 2007/0156093 A1 | 7/2007 | Woehr |
| 2007/0270753 A1 | 11/2007 | Kulli |
| 2007/0276288 A1 | 11/2007 | Khaw |
| 2008/0065015 A1 | 3/2008 | Fiser et al. |
| 2008/0125709 A1 | 5/2008 | Chang et al. |
| 2008/0300574 A1 | 12/2008 | Belson et al. |
| 2009/0082732 A1 | 3/2009 | Hillman |
| 2009/0143738 A1 | 6/2009 | Hendriksen et al. |
| 2009/0163861 A1 | 6/2009 | Carlyon |
| 2009/0163871 A1 | 6/2009 | Burkholz et al. |
| 2009/0177114 A1 | 7/2009 | Chin et al. |
| 2009/0247986 A1 | 10/2009 | Rioux et al. |
| 2009/0247994 A1 | 10/2009 | Bacher et al. |
| 2009/0299291 A1 | 12/2009 | Baid |
| 2009/0312711 A1 | 12/2009 | Brimhall |
| 2010/0042076 A1 | 2/2010 | McCarthy et al. |
| 2010/0087755 A1 | 4/2010 | Boezaart |
| 2010/0094310 A1 | 4/2010 | Warring et al. |
| 2010/0168756 A1 | 7/2010 | Dorn et al. |
| 2010/0191188 A1 | 7/2010 | Harding et al. |
| 2010/0191189 A1 | 7/2010 | Harding et al. |
| 2010/0191224 A1 | 7/2010 | Butcher |
| 2010/0204654 A1 | 8/2010 | Mulholland et al. |
| 2010/0249707 A1 | 9/2010 | Woehr et al. |
| 2011/0009849 A1 | 1/2011 | Christensen et al. |
| 2011/0213307 A1 | 9/2011 | Kawai et al. |
| 2011/0282280 A1 | 11/2011 | Fiser et al. |
| 2011/0282285 A1 | 11/2011 | Blanchard et al. |
| 2011/0288482 A1 | 11/2011 | Farrell et al. |
| 2011/0319825 A1 | 12/2011 | Goral et al. |
| 2011/0319838 A1 | 12/2011 | Goral et al. |
| 2012/0053523 A1 | 3/2012 | Harding |
| 2012/0059247 A1 | 3/2012 | Speeg et al. |
| 2012/0078200 A1 | 3/2012 | Woehr et al. |
| 2012/0089094 A1 | 4/2012 | Franer et al. |
| 2012/0095404 A1 | 4/2012 | Massengale et al. |
| 2012/0116248 A1 | 5/2012 | Mcweeney et al. |
| 2012/0123339 A1 | 5/2012 | Abe et al. |
| 2012/0172806 A1 | 7/2012 | Woehr et al. |
| 2012/0179104 A1 | 7/2012 | Woehr et al. |
| 2012/0184910 A1 | 7/2012 | Woehr |
| 2012/0197200 A1 | 8/2012 | Belson |
| 2012/0203181 A1 | 8/2012 | Woehr et al. |
| 2012/0215171 A1 | 8/2012 | Christiansen |
| 2012/0220942 A1 | 8/2012 | Hall et al. |
| 2012/0220956 A1 | 8/2012 | Kuracina et al. |
| 2012/0271235 A1 | 10/2012 | Fuchs et al. |
| 2012/0271247 A1 | 10/2012 | Weaver et al. |
| 2012/0277679 A1 | 11/2012 | Steube |
| 2012/0283553 A1 | 11/2012 | Cully et al. |
| 2013/0006101 A1 | 1/2013 | McHugo et al. |
| 2013/0030372 A1 | 1/2013 | Franer et al. |
| 2013/0046315 A1 | 2/2013 | Woehr et al. |
| 2015/0051574 A1 * | 2/2015 | Tan ............... A61M 5/2053 604/500 |
| 2015/0051584 A1 | 2/2015 | Korkuch et al. |
| 2016/0331929 A1 | 11/2016 | Lampropoulos et al. |
| 2016/0331938 A1 | 11/2016 | Blanchard et al. |

(56) References Cited

U.S. PATENT DOCUMENTS

| | | | |
|---|---|---|---|
| 2016/0331940 A1 | 11/2016 | Ishida | |
| 2018/0280663 A1 | 10/2018 | Ishida | |
| 2019/0022358 A1 | 1/2019 | Belson | |

FOREIGN PATENT DOCUMENTS

| | | |
|---|---|---|
| CN | 101138483 A | 3/2008 |
| CN | 102440840 A | 5/2012 |
| CN | 102939129 A | 2/2013 |
| CN | 103124531 A | 5/2013 |
| CN | 103379937 A | 10/2013 |
| CN | 105073174 A | 11/2015 |
| CN | 105611962 A | 5/2016 |
| CN | 106456878 A | 2/2017 |
| CN | 106456879 A | 2/2017 |
| EP | 0382190 A2 | 8/1990 |
| EP | 0386936 A1 | 9/1990 |
| EP | 0592720 A1 | 4/1994 |
| EP | 0475857 B1 | 3/1995 |
| EP | 0599564 B1 | 1/1997 |
| EP | 0815887 A2 | 1/1998 |
| EP | 0545671 B1 | 3/1999 |
| EP | 0747085 B1 | 3/2000 |
| EP | 0722749 B1 | 2/2001 |
| EP | 1378261 A1 | 1/2004 |
| EP | 1459781 A1 | 9/2004 |
| EP | 0964716 B1 | 8/2005 |
| EP | 1726326 A2 | 11/2006 |
| EP | 2433670 A1 | 3/2012 |
| JP | 9108348 A | 4/1997 |
| JP | 11-502131 A | 2/1999 |
| JP | 2008-148737 | 7/2008 |
| JP | 2010-512803 A | 4/2010 |
| JP | 2013527005 A | 6/2013 |
| JP | 2013-529111 A | 7/2013 |
| JP | 2016530934 A | 10/2016 |
| WO | 97/21458 A1 | 6/1997 |
| WO | 02/066093 A2 | 8/2002 |
| WO | 2007/003874 A1 | 1/2007 |
| WO | 2007006055 A2 | 1/2007 |
| WO | 2008/005618 A2 | 1/2008 |
| WO | 2010012023 A1 | 2/2010 |
| WO | 2010078151 A1 | 7/2010 |
| WO | 2011/143621 A1 | 11/2011 |
| WO | 2013180234 A1 | 12/2013 |
| WO | 2015023358 A1 | 2/2015 |
| WO | 2015115316 A1 | 8/2015 |
| WO | 2016/185950 A1 | 11/2016 |

\* cited by examiner

CATHETER INSERTION DEVICE

CROSS-REFERENCE TO RELATED APPLICATIONS

This application is a continuation of U.S. patent application Ser. No. 15/950,507, filed on Apr. 11, 2018, now U.S. Pat. No. 10,737,063 issued on Aug. 11, 2020, which claims the benefit of U.S. Provisional Patent Application No. 62/485,167, filed on Apr. 13, 2017, the disclosures of which are hereby incorporated by reference in their entirety.

TECHNICAL FIELD

This disclosure generally relates to medical devices for use in the insertion of catheters or other medical equipment into the vasculature of a patient. More particularly, this disclosure relates to a catheter insertion device for at least partial insertion of a catheter within the vasculature of the patient.

BACKGROUND

Different types of medical devices, such as needles, introducers, trocars, catheters, stents, angiography balloons, cutting tools, and imaging tools can be introduced into the body for various medical procedures. For example, catheters are used to introduce or remove fluids from vessels in the body for a variety of medical procedures. In a typical procedure, to insert a catheter in a vessel, the vessel access is first verified by aspiration using a long hollow needle, such as a syringe needle. A guidewire is then passed through the needle into the vessel. The guidewire acts as a track for the catheter to pass over to reach a target location within the vessel. A catheter is finally passed over the guidewire to the target location in the vasculature of the patient. With the catheter in place, the needle and the guidewire are removed, leaving only the catheter in the vessel. Fluids are then introduced or removed from the vessel through the catheter by connecting a fluid source or aspiration device to the catheter hub.

Various devices are known for placement of a catheter in the vasculature of a patient. Maintaining sterility of the various components of the device by, for example, preventing the contact of the fingers of the operator with the various parts of the needle, the guidewire, and the catheter itself during operation, is important for use of these devices. However, conventional catheter placement devices typically require the use of two hands for the insertion of the guide wire and advancement of the catheter into the vasculature, which increases the risk of contamination and also increases the risk of inadvertently damaging the vessel due to unintended needle point movement. Moreover, conventional catheter placement devices also prevent the continuous use of ultrasound from the point of skin penetration, vessel access, and wire guide insertion, through to having the first distal portion of the catheter in the vessel and needle point shielded. This makes such conventional catheter placement devices less convenient for use. Additionally, the aforementioned drawbacks of conventional catheter placement devices affect the success rate of insertion into the vasculature.

Therefore, a need exists for a novel catheter insertion device that allows for single-handed insertion of the catheter within the vasculature of the patient. Additionally, a need exists for a catheter insertion device that allows for easy, safe, and fast catheter placement into a patient's vasculature.

SUMMARY

The foregoing needs are met, to a great extent, by implementations of a catheter insertion device according to the present disclosure. In accordance with one implementation, a catheter insertion device may include a handle having a proximal body portion and two cantilever arms each extending distally from said body portion; a needle cannula having a proximal end located within the handle proximal body portion, said needle cannula extending distally from the handle proximal body portion and defining a distal cantilever portion disposed partially between the two cantilever arms of the handle; a catheter assembly removably coupled to the handle and configured to slide on the needle cannula, the catheter assembly comprising an elongated catheter, a catheter hub connected to a proximal end of the elongated catheter, and a catheter advancer base connected to the catheter hub; and a needle support having two parallel walls pivotally connected to the handle, said needle support pivoting between a first position and second position, said needle support configured to support the needle cannula on the cantilever portion of said needle cannula when the needle support is in the first position and said needle cannula is disposed between said two parallel walls of the needle support, said needle support blocking distal advancement of the catheter assembly when said needle support is in the first position.

In some implementations, the catheter insertion device may comprise a guidewire and a guidewire actuator for extending or retracting the guidewire, wherein the needle support cannot pivot away from the first position before the guidewire actuator is moved to extend the guidewire distally past a tip of the needle cannula.

In some implementations, the two arms of the handle comprise a top arm and a bottom arm, and the catheter advancer base slidably engages the bottom arm of the handle.

In some implementations, the catheter advancer base may include a guide track configured to receive the bottom arm of the handle for moving the catheter assembly in a distal direction relative to the handle and in a proximal direction relative to the handle, and wherein the guide track prevents twisting of the catheter assembly during movement of the catheter assembly in both the distal and proximal directions.

In some implementations, the catheter advancer base may include a pair of grip arms for supporting a choked up hand position by a user.

In some implementations, the needle support is pivotally connected to a distal portion of the top arm of the handle and configured to move relative to the handle upon abutment of the catheter advancer base to the needle support.

In some implementations, the needle support is configured to pivot relative to the handle about a pivot axis perpendicular to an axis of the needle cannula.

In some implementations, the needle support may further comprise a hook portion configured to releasably mate with the bottom arm of the handle when said needle portion is in the first position.

In some implementations, moving the guidewire actuator in a proximal direction relative to the handle causes a distal end of the guidewire to move in a distal direction away from the handle, and moving the guidewire actuator in a distal direction relative to the handle causes the distal end of the guidewire to move in a proximal direction towards the handle.

In some implementations, the catheter insertion device may comprise a catheter assembly actuator connected to the handle, the catheter assembly actuator being movable relative to the handle to push the catheter assembly distally relative to the handle.

In some implementations, the catheter advancer base may further comprise a seat portion configured to stably secure the catheter and catheter hub.

In some implementations, the catheter advancer base may further comprise a retaining member configured to secure the catheter hub.

In some implementations, the needle support may further comprise a textured surface to aid gripping.

In some implementations, the needle cannula may further comprise a sharp distal tip extending distally from the handle, the distal tip having a back-grind portion defining a gradual taper.

In some implementations, the guidewire further has a variable stiffness.

In some implementations, the needle cannula further comprises a swage having an oval-shaped cross section bulge near a distal tip of the needle cannula.

In some implementations, a catheter insertion device comprises: a handle having a body portion and an arm extending distally from the body portion; a needle cannula partially within the handle, the needle cannula comprising a sharp distal tip extending distally from the handle; a catheter assembly removably coupled to the handle, the catheter assembly comprising an elongated catheter, a catheter advancer base having a seat portion, and a catheter hub connected to the elongated catheter and matingly received in the seat portion of the catheter advancer base; and a needle support connected to the handle and movable between a first position and a second position, the needle support configured to stabilize lateral movement of the needle cannula when in the first position, and the needle support configured to block distal advancement of the catheter assembly when in the first position.

In some implementations, the needle support is configured to permit distal advancement of the catheter assembly when in the second position.

In some implementations, the catheter insertion devices further comprises a guidewire partially disposed within the handle, and a first actuator connected to the handle and the guidewire, the first actuator movable between an extended position where the first actuator abuts the needle support when the needle support is in the first position, and a retracted position where the first actuator does not abut the needle support when the needle support is in the first position, and wherein moving the first actuator between the extended and retracted positions causes the guidewire to move relative to the handle.

In some implementations, the catheter insertion device further comprises a second actuator connected to the handle and configured to move the catheter assembly distally relative to the handle and move the needle support from the first position to the second position when the first actuator does not abut the needle support.

Certain implementations of the catheter insertion device have been outlined so that the detailed description below may be better understood. There are, of course, additional implementations that will be described below and which will form the subject matter of the claims. In this respect, it is to be understood that the catheter insertion device is not limited in its application to the details of construction and to the arrangements of the components set forth in the following disclosure or illustrated in the drawings. Also, it is to be understood that the phraseology and terminology employed herein are for the purpose of description and should not be regarded as limiting. As such, the conception upon which this disclosure is based may readily be utilized as a basis for the designing of other structures, methods, and systems for carrying out the several purposes of the catheter insertion device. It is understood, therefore, that the claims include such equivalent constructions insofar as they do not depart from the spirit and scope of the present disclosure.

BRIEF DESCRIPTION OF THE DRAWINGS

Implementations of the catheter insertion device are described with reference to the drawings, in which like reference numerals refer to like parts throughout.

DETAILED DESCRIPTION

Figure 1A:
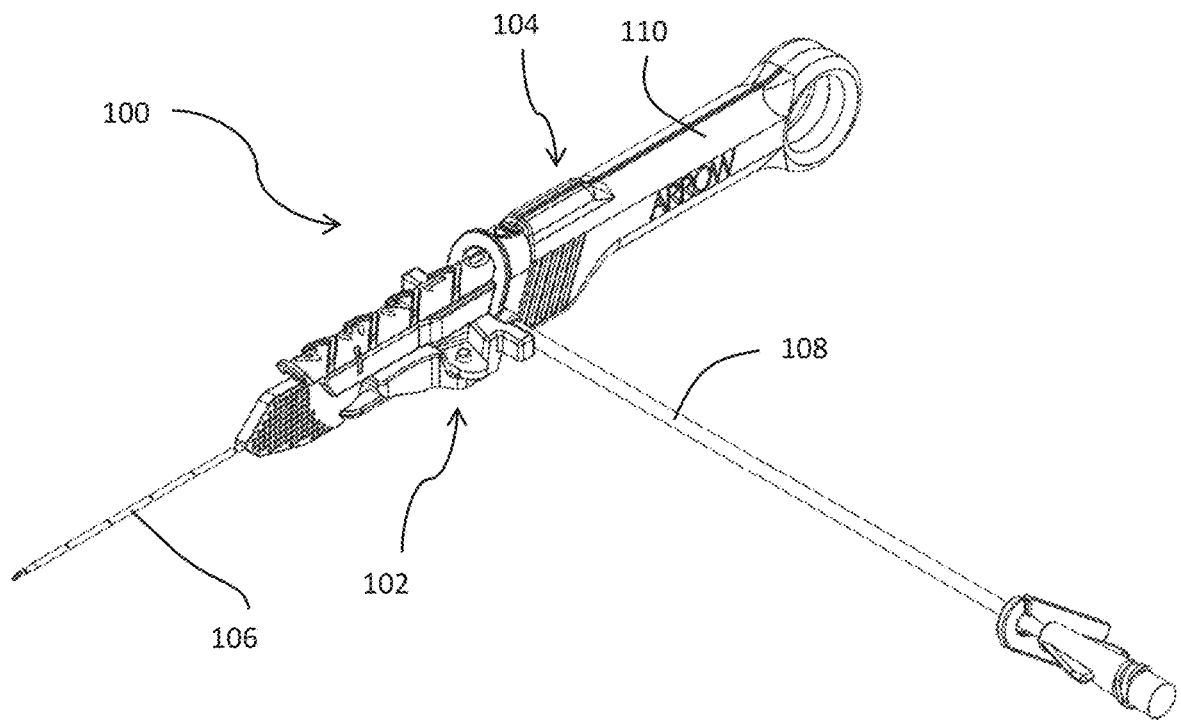
FIG. 1A illustrates a top perspective view of an implementation of a catheter insertion device including a catheter group and an insertion group.
Figure 1B:
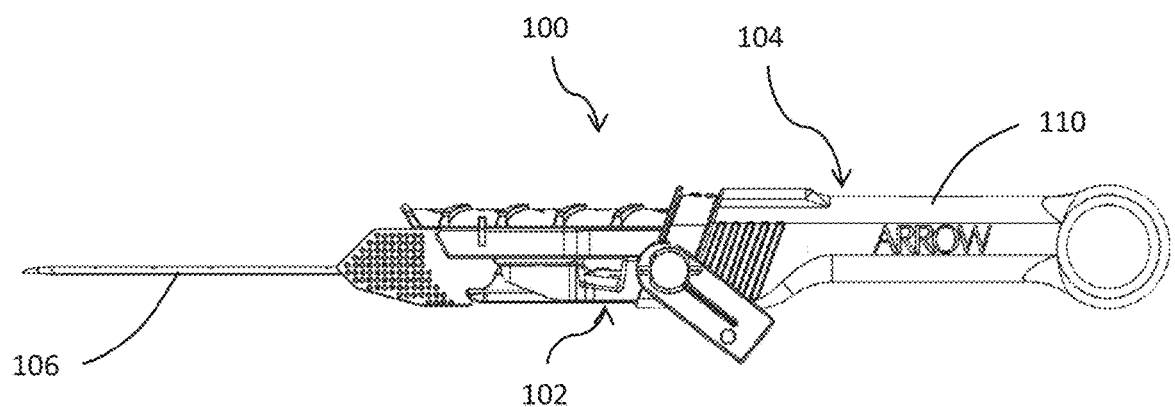
FIG. 1B illustrates a side elevation view of the catheter insertion device of FIG. 1A.

Referring to FIGS. 1A and 1B, an implementation of a catheter insertion device 100 including a catheter group 102 and an insertion group 104 is illustrated. The insertion group 104 may be separated from the catheter group 102 following partial insertion of a catheter 106 in the vasculature of a patient. The catheter group 102 also includes an extension line assembly 108 in fluid communication with the catheter 106. The extension line assembly 108 may be connected to a fluid source or an aspiration device. The insertion group 104 includes a handle 110 that is initially connected to the catheter group 102 and that facilitates the insertion of the catheter 106 in the vasculature of the patient.

Figure 2A:
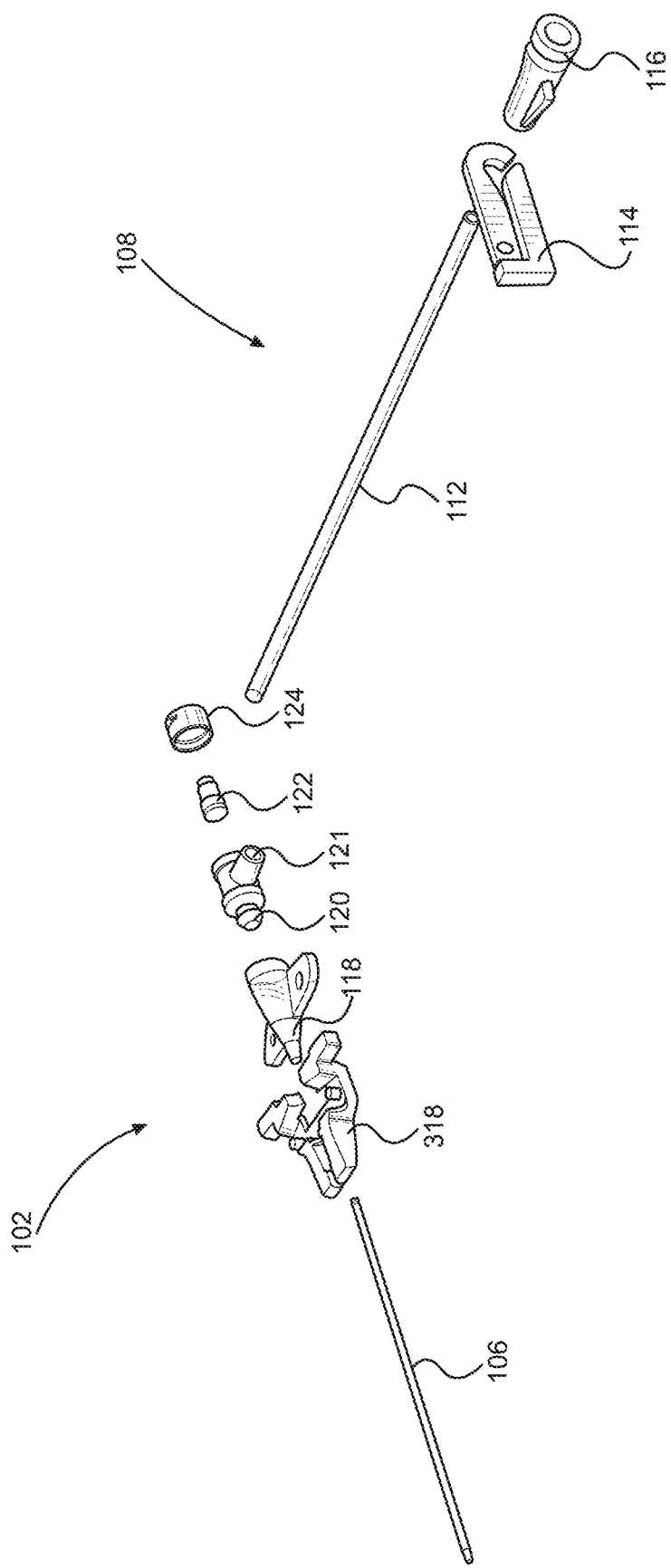
FIG. 2A illustrates an exploded view of the separate components of the catheter group of the catheter insertion device.
Figure 2B:
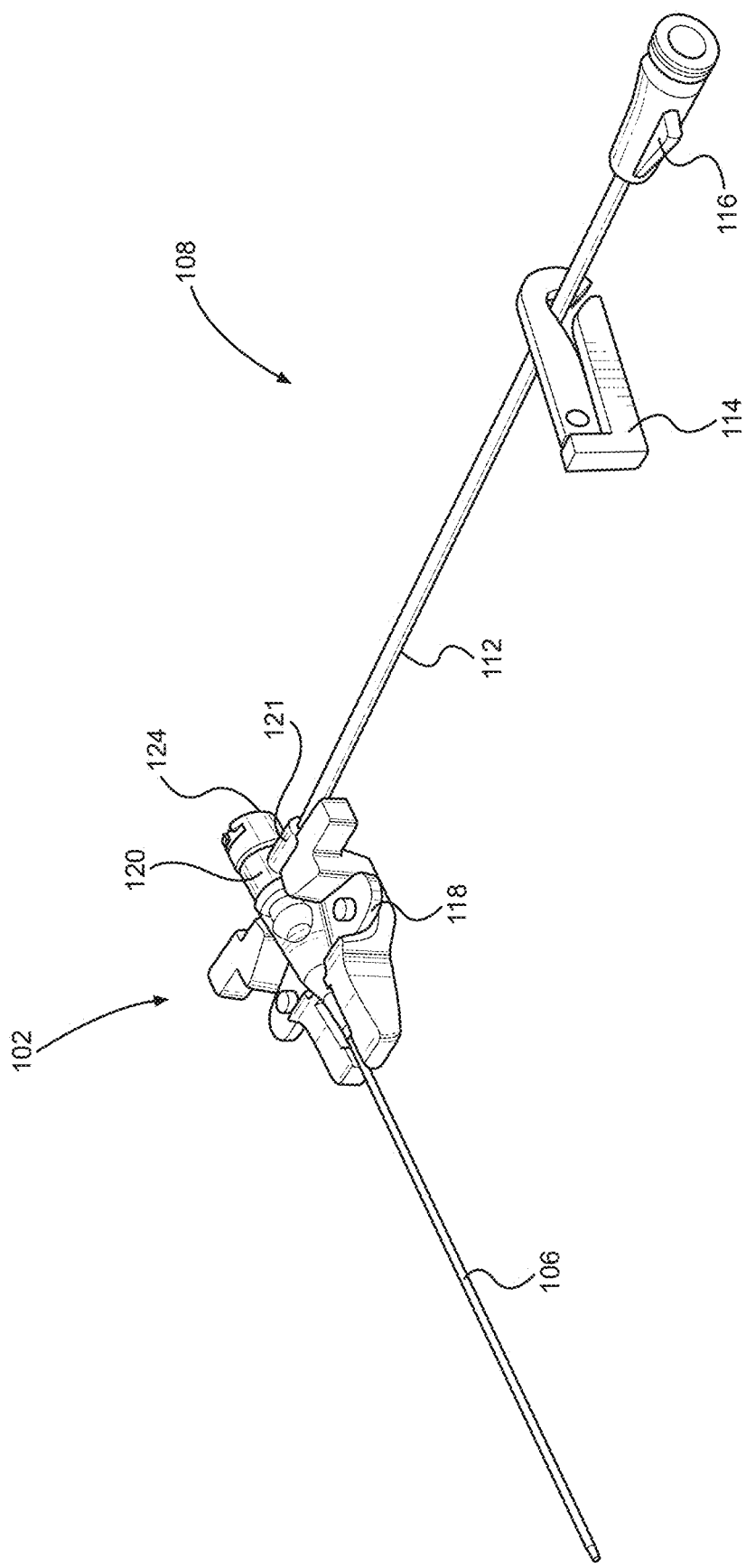
FIG. 2B illustrates a partially transparent perspective view of the assembled catheter group of the catheter insertion device.

FIG. 2A illustrates an exploded view of the separate components of the catheter group 102 of the catheter insertion device 100. Referring to FIG. 2B, a partially transparent perspective view of the assembled catheter group 102 of the catheter insertion device 100 is illustrated. At its proximal region, the catheter group 102 includes an extension line assembly 108 that includes an elongated extension line 112, an extension line clamp 114, and an extension line hub 116. A vent plug, as shown in FIG. 1A, may further be attached to the extension line hub 116 during insertion of the needle and then removed prior to use by the practitioner, i.e. before the practitioner connects a syringe to the extension line hub 116. The elongated extension line 112 defines an elongated lumen that is in fluid communication with the lumen defined by the catheter 106 through the lumen defined by a rigid hub 120. The extension line clamp 114 is received around the elongated extension line 112 and may be slid in a direction perpendicular to the longitudinal axis of the elongated extension line 112 to pinch the elongated extension line 112 closed. When the extension line clamp 114 pinches the elongated extension line 112, fluid is prevented from flowing beyond the extension line clamp 114 either distally towards the catheter 106 or proximally towards the extension line hub 116. The extension line hub 116 defines a lumen that is in fluid communication with the lumen defined by the elongated extension line 112.

In some implementations, the lumen defined by the extension line hub 116 may be tapered from its proximal end towards its distal end, while in other implementations, the lumen defined by the extension line hub 116 may have a uniform diameter. The proximal end of the extension line hub 116 includes a connector, such as a threaded luer lock, for connection to a fluid source or an aspiration device. The fluid source may be a syringe or an intravenous bag, among others.

At its distal end, the catheter group 102 includes the elongated catheter 106 that is connected to a catheter hub 118. In particular, the proximal end of the elongated catheter 106 connects to the distal end of the catheter hub 118. The rigid hub 120 is partially received within the proximal end of the catheter hub 118. The rigid hub 120 receives a seal 218 that acts as a valve within an internal cavity defined by the rigid hub 120. The proximal end of the rigid hub 120 is sealed by a rigid hub cap 124. The proximal end of the rigid hub cap 124 has an opening that allows the needle cannula 130 and the guidewire 132 to pass through the rigid hub cap 124 to the seal 218. The elongated catheter 106 defines an elongated lumen that is at least partially received within the vasculature of the patient. The catheter hub 118 defines a tapered cavity that is in fluid communication with the lumen defined by the elongated catheter 106 and the lumen defined by the rigid hub 120. The rigid hub 120 also includes a side port 121 for receiving the elongated extension line 112 of the extension line assembly 108. The lumen defined by the side port 121 is in fluid communication with the lumen defined by the elongated extension line 112.

The seal 218 is a multi-piece seal, as described in greater detail below. In other implementations, the seal may be one-piece seal, as described in U.S. patent application Ser. No. 14/306,698, filed Jun. 17, 2014, the full disclosure of which is incorporated herein by reference in its entirety.

When the catheter group 102 is assembled, the seal 218 is enclosed by the rigid hub 120 and the rigid hub cap 124. In some implementations, the catheter group 102 may not include the extension line assembly 108 and the fluid source or aspiration device can be connected to a proximal end of the rigid hub 120.

Figure 3A:
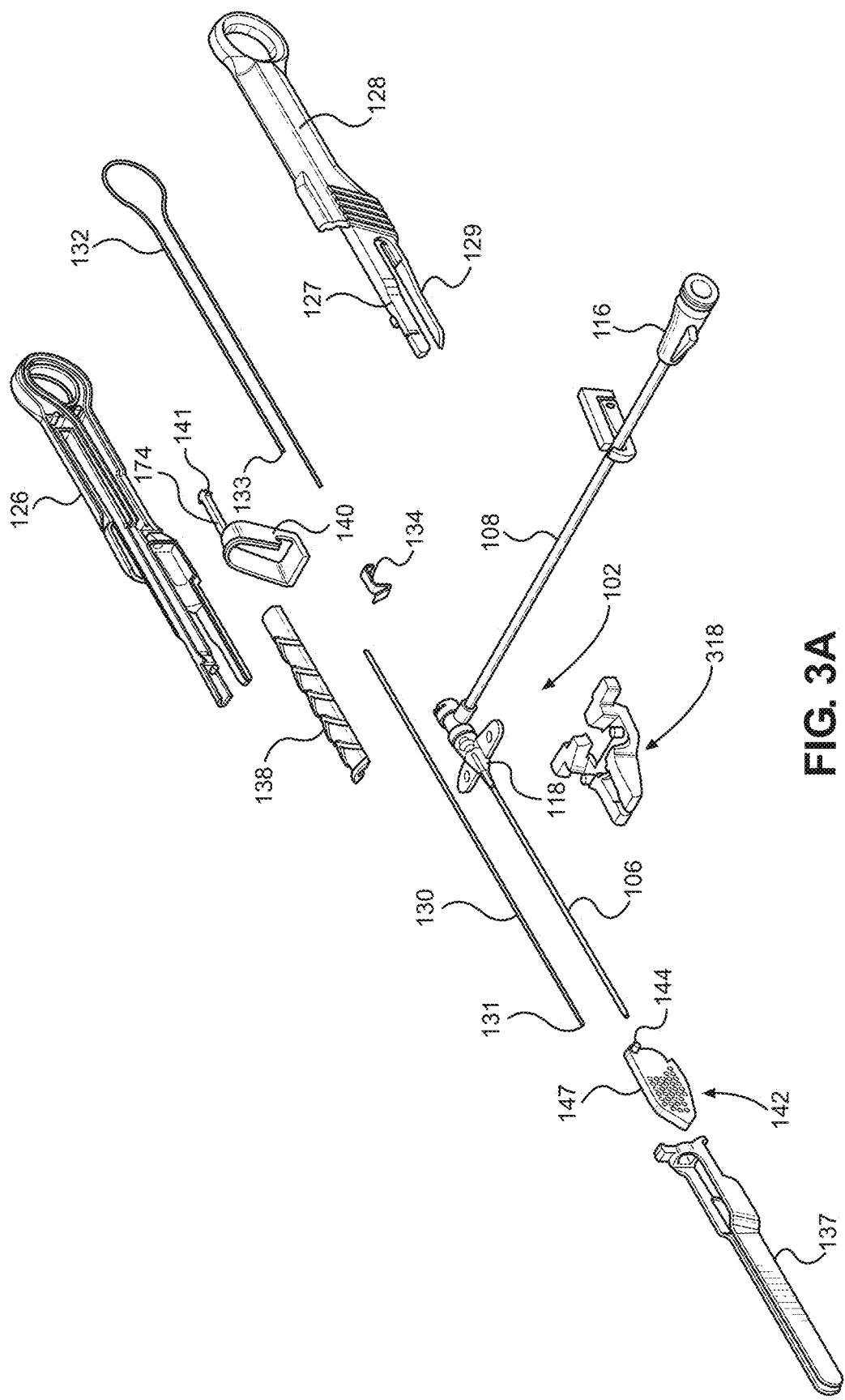
FIG. 3A illustrates a partially exploded view of the catheter insertion device.
Figure 3B:
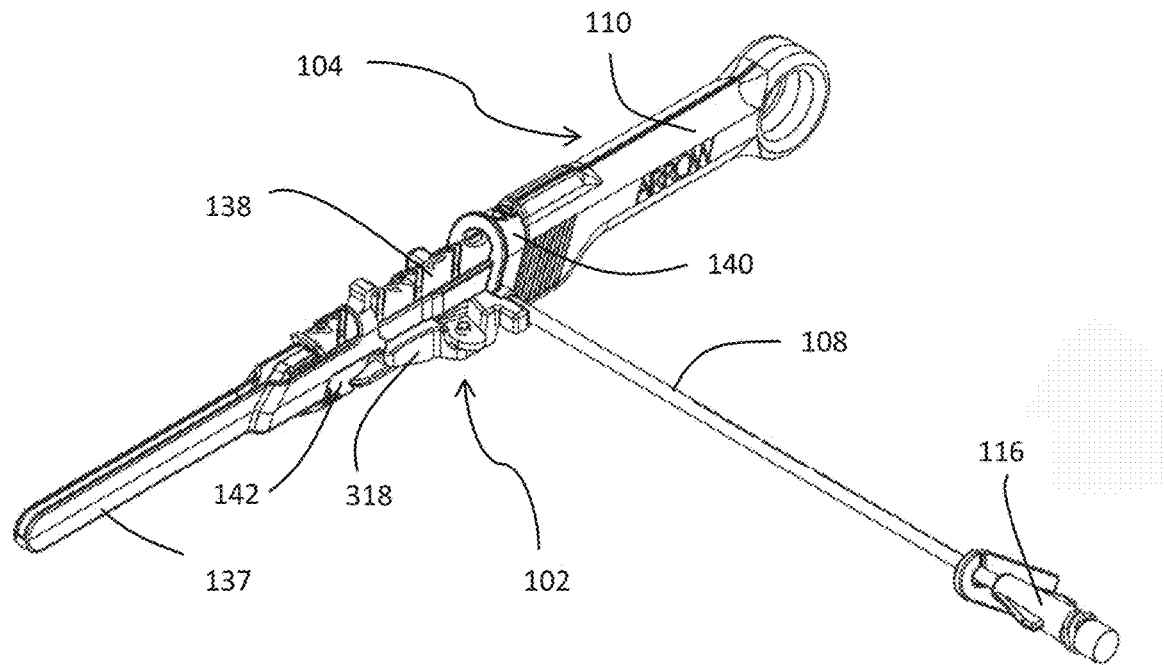
FIG. 3B illustrates a top perspective view of the catheter insertion device having a protective needle guard.
Figure 3C:
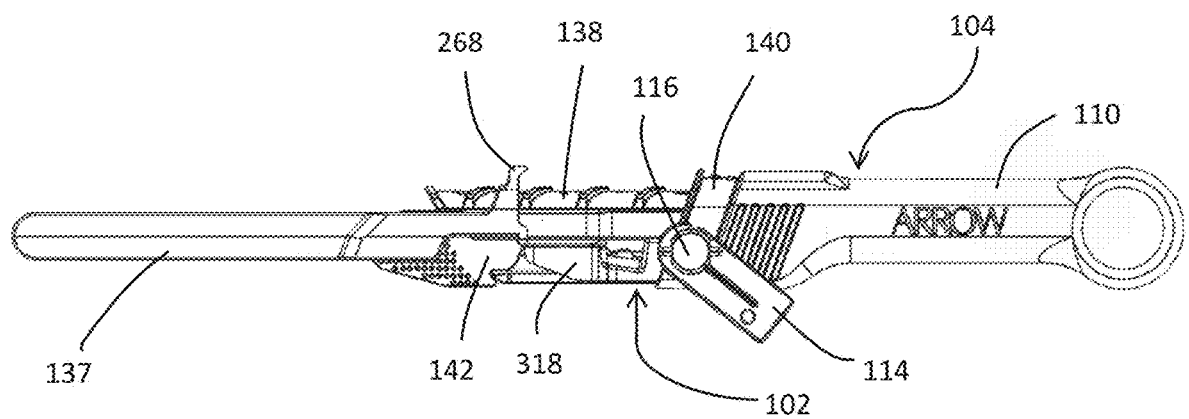
FIG. 3C illustrates a side elevation view of the catheter insertion device having a protective needle guard.

Referring to FIG. 3A, an exploded view of the separate components of the insertion group 104 of the catheter insertion device 100 is illustrated along with an assembled view of the catheter group 102. FIGS. 3B and 3C illustrate a perspective view and a side view, respectively, of the assembled catheter group 102 and insertion group 104 of the catheter insertion device 100. The insertion group 104 includes the handle 110 that is made up of a right housing 126 and a left housing 128 that are connected together. Top arm 127 and bottom arm 129 are formed in the distal region of the handle 110. A needle cannula 130 is held within the handle 110 and a guidewire 132, which slides through the lumen defined by the needle cannula 130, is also held within the handle 110. The needle cannula 130 may be anchored within the handle 110 by an interference fit within an inner channel defined by the handle 110, by an adhesive, by a threaded connection, or the like. In some implementations, the needle cannula 130 may be, for example, a 24 gauge needle.

A needle safety clip 134 is placed around the outer surface of the needle cannula 130 to cover the sharp needle tip 131 following separation of the insertion group 104 from the catheter group 102. A needle guard 137 covers the portion of the needle cannula 130 extending from the handle 110 before initial use of the catheter insertion device 100. A first actuator, such as a slider 138, is connected to the top of the handle 110 and to the guidewire 132 and slides the guidewire 132 relative to the handle 110 in both proximal and distal directions. In some implementations, the guidewire 132 may be a spring wire guide, such as a coiled or a coil-less spring wire guide. The length of the guidewire 132 is selected such that, before the slider 138 is actuated, the distal end of the guidewire does not extend beyond the sharp needle tip 131 of the needle cannula 130.

The guidewire 132 may have a variable stiffness, as discussed in further detail below. In some implementations, the guidewire 132 may have an outer diameter that is substantially uniform and less than or equal to 0.010 inches (0.0254 centimeters). Preferably, the guidewire 132 has an outer diameter that is less than or equal to 0.010 inches when the needle cannula 130 is a 24 GA needle and the elongated catheter 106 is a 22 GA catheter, so that the guidewire 132 may fit within the lumen defined by the 22 GA catheter. In other implementations, the guidewire 132 may have a varying diameter that narrows distally, such that the diameter of the guidewire 132 is the smallest at a distal end of the guidewire 132. When the guidewire 132 is fully advanced, the larger diameter section is immediately distal to the needle 130, which helps to guide the catheter 106 during advancement and also directs the catheter's movement during the initial part of the advancement. Further, the distal tip of the guidewire 132 has a small outer diameter so that it is sufficiently flexible to help the guidewire 132 travel a tortuous path out of the needle 130 and into the lumen of the vessel. The guidewire also comprises a large diameter tip, such as a tip shaped like a ball so that it is not sharp. Such a large ball-shaped tip helps the clinician determine whether the entire guidewire is removed after use, since the clinician can see if the ball is there, thus indicating that no piece of the guidewire was left behind. Moreover the ball-shaped tip at the distal end of the guidewire 132 is not sharp so as to avoid puncturing a patient's vasculature during operation.

In some implementations, the guidewire 132 may be made of a metal, such as a metal alloy. For example, the guidewire 132 may be made of an alloy of nickel and titanium. In some implementations, the guidewire 132 may be coated with polysulfones, polyfluorocarbons, polyolefins, polyesters, polyurethanes, blends and/or copolymers.

A second actuator, such as a release 140, is also connected to the handle 110 of the insertion group 104 and to the catheter group 102. The release is configured to slide the catheter group 102 relative to the handle 110 in a distal direction. The release 140 includes a proximal arm 174 having an enlarged proximal end 141. A needle support 142 is attached to a proximal region of the handle 110 and swings upward and downward relative to the handle 110. In particular, the needle support 142 is rotationally coupled to the top arm 127 by a pivot member 144.

Figure 3D:
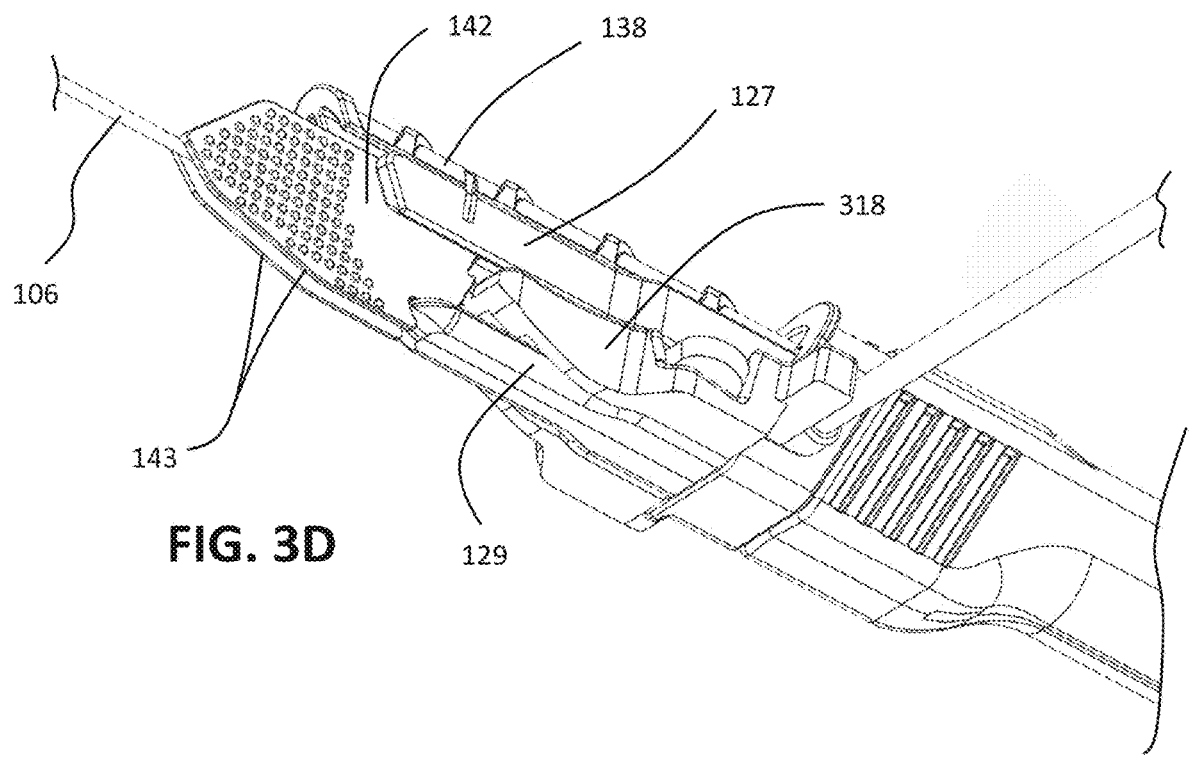
FIG. 3D illustrates an enlarged bottom perspective view of a portion of the catheter insertion device.

A catheter advancer base 318 is removably connected to the catheter hub 118 and configured to slidably engage the bottom arm 129 of the handle 110, as illustrated in FIG. 3D. The needle support 142 may comprise a rigid plastic material to support the needle cannula 130 from bending during insertion into a patient's vasculature. The needle support 142 includes two parallel walls 143 separated by a distance slightly greater than the outer diameter of the elongated catheter 106 in which the needle cannula 130 passes in order to stabilize lateral movement of the needle cannula 130 during insertion of the needle in the vasculature of the patient. This stabilization is especially important for insertion of the needle relatively deep in the tissue of the patient, such as within an organ of the patient. Additionally, the needle support may further include a textured outer surface to aid gripping by a practitioner during insertion of the catheter into the vasculature of a patient. Examples of such a textured outer surface include various patterns of protrusions, divots, grooves, channels and bumps, among others. In other implementations, the textured surface may be formed of a different material, such as rubber, or may be formed as a roughened surface directly on the needle support 142. In some implementations, such examples of a textured surface may also be added to regions of the catheter advancer base 318, such as to a grip arm 321 or grip recess 322, among other areas, in order to aid with gripping.

Figure 3E:
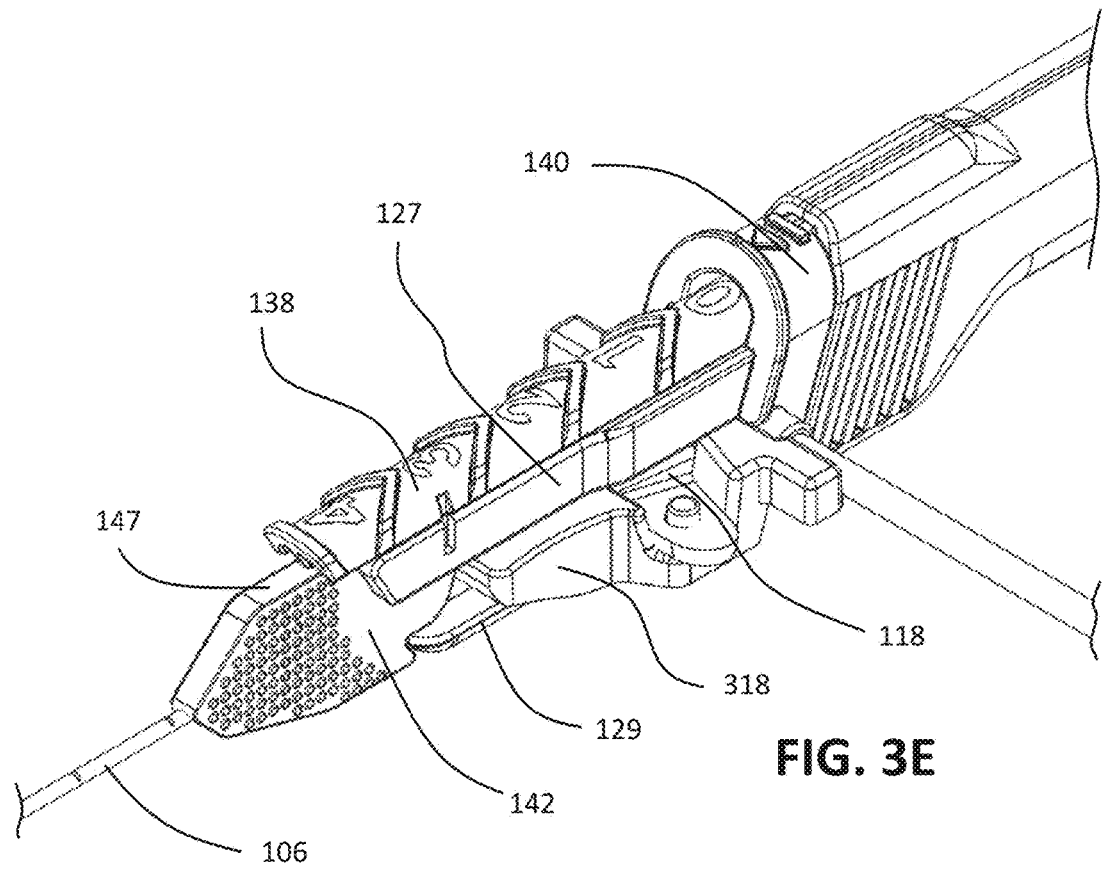
FIG. 3E illustrates an enlarged top perspective view of a portion of the catheter insertion device.
Figure 3F:
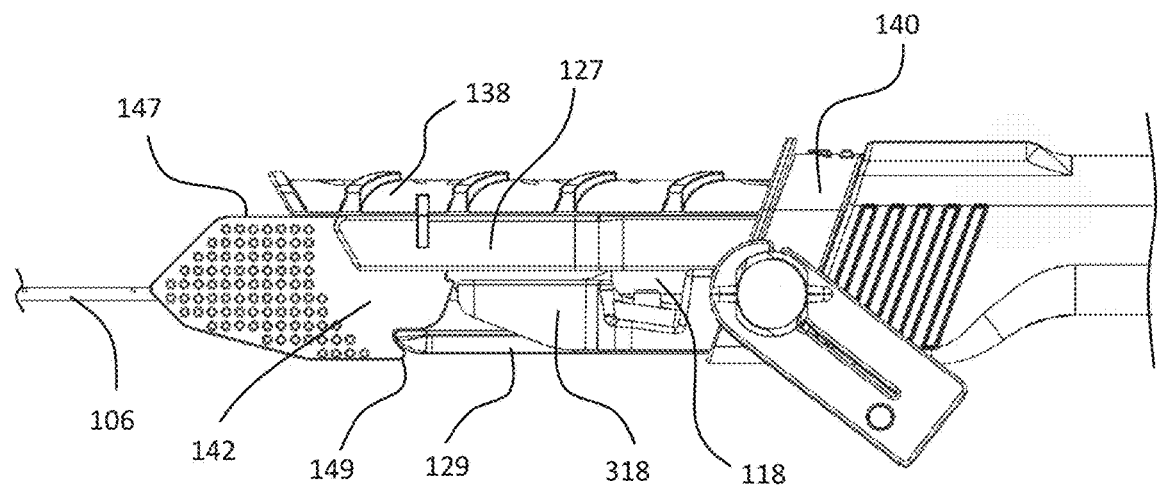
FIG. 3F illustrates an enlarged side elevation view of a portion of the catheter insertion device.

As illustrated in FIGS. 3E and 3F, the needle support 142 also includes a top portion 147 that abuts the bottom surface of the slider 138 before the slider is slid proximally in order to prevent swinging of the needle support 142 while the catheter insertion device 100 is being inserted in the vasculature of the patient. A lip 149 may be provided on the needle support 142 that defines a seat region configured to hook around a distal end of the bottom arm 129 of the housing in order to prevent the needle 130 and/or the catheter 106 from popping out of the needle support 142 prematurely. Further, the needle support 142 may comprise a trapezoidal or other geometric shape, and may have an extended longitudinal length, for example 2 cm, configured to provide additional support to the catheter.

Figure 3H:
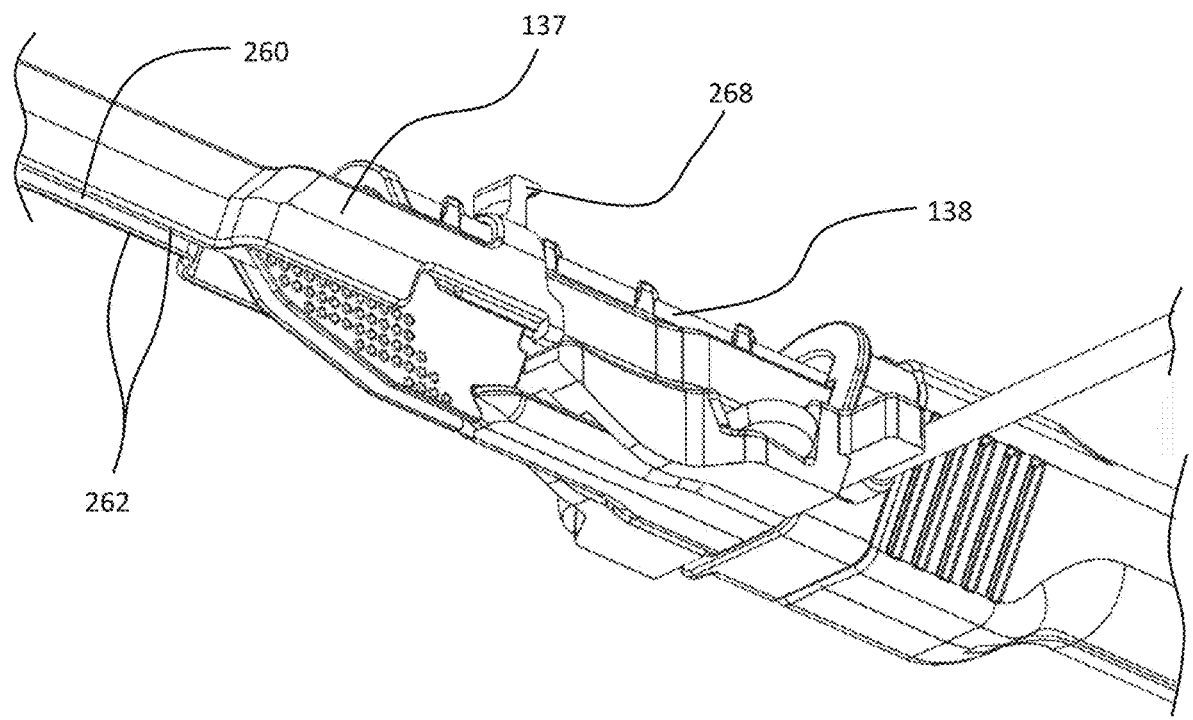
FIG. 3H illustrates an enlarged bottom perspective view of a portion of the catheter insertion device having a protective needle guard.
Figure 3G:
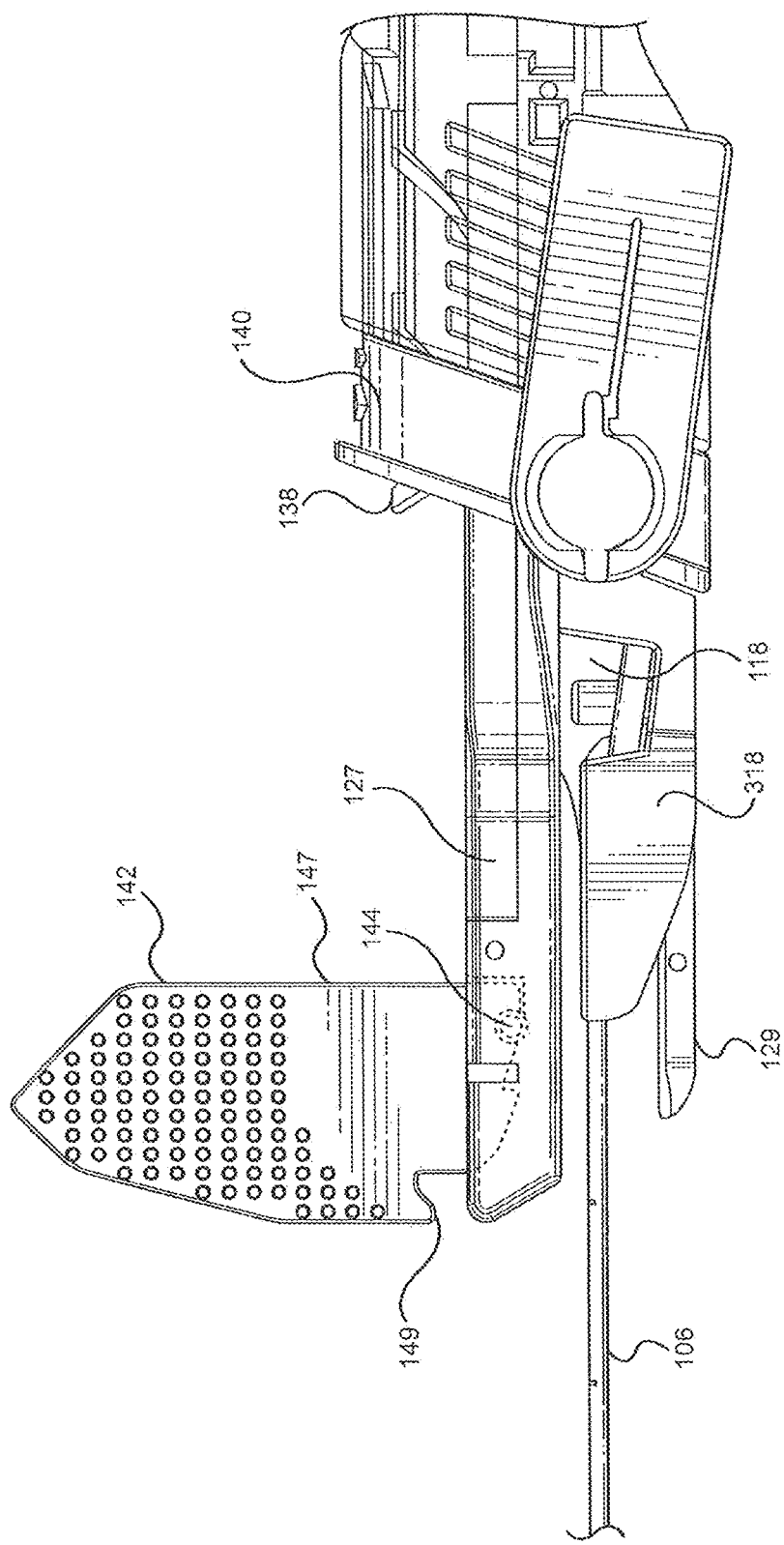
FIG. 3G illustrates the catheter insertion device having a slider in a retracted position and a needle support in an upright position.

As shown in FIG. 3G, the needle support 142 is free to swing about a pivot member 144 when the slider 138 is retracted to the extent in which it no longer abuts the top portion 147 of the needle support. The catheter advancer base 318 is configured to receive the catheter hub 118 of the catheter group 102, as will be discussed in greater detail below. A retaining member, such as a protruding clip 323, is provided on the catheter advancer base 318 and is configured to further secure the wings of the catheter hub 118 to help retain the catheter hub 118 to the catheter advancer base 318 during deployment.

Referring to FIG. 3H, the needle guard 137 includes an open channel 260 defined by two parallel side walls 262. A bottom longitudinal feature and a top longitudinal feature between the parallel side walls 262 secure around the needle cannula 130. As such, the bottom and top longitudinal features are spaced apart by a distance slightly greater than the outer diameter of the catheter 106. A tab 268 may be provided at the proximal end of the needle guard 137 to allow the practitioner to initially lift the needle guard 137 out of contact with the slider 138, and then push the needle guard 137 distally until the proximal ends of the bottom and top longitudinal features are distal of the sharp needle tip 131. At this point, the needle guard 137 disengages from the insertion group 104 and may be removed to expose the sharp needle tip 131.

Figure 4A:
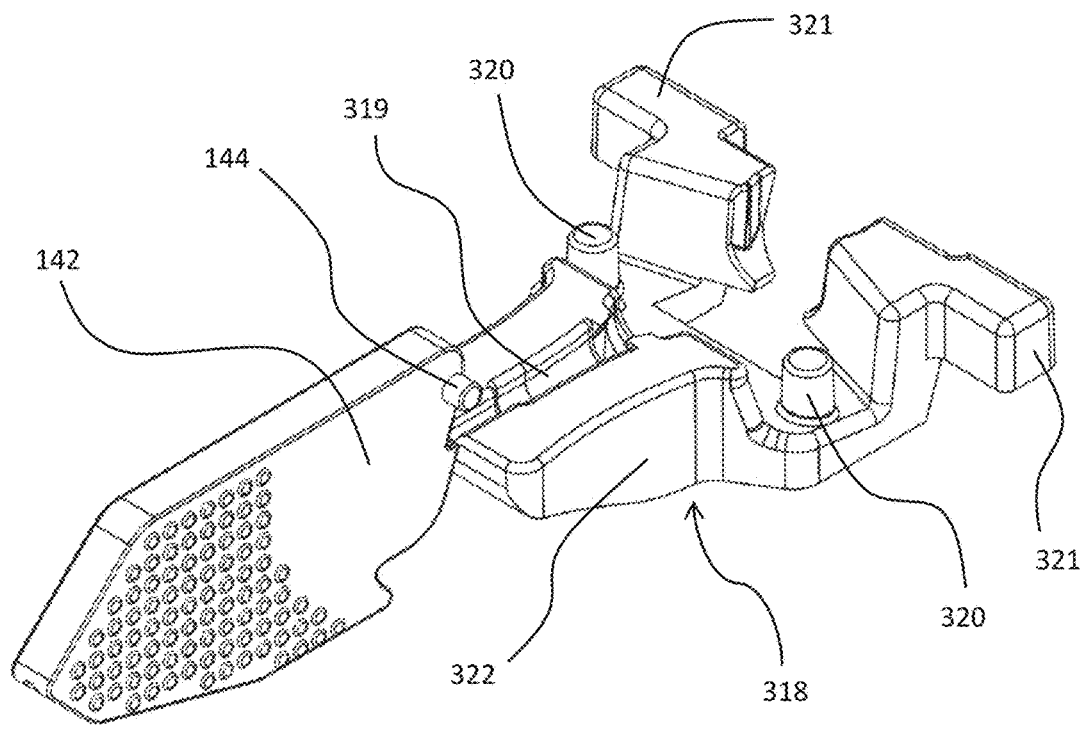
FIG. 4A illustrates a top perspective view of a catheter advancer base and a needle support.
Figure 4B:
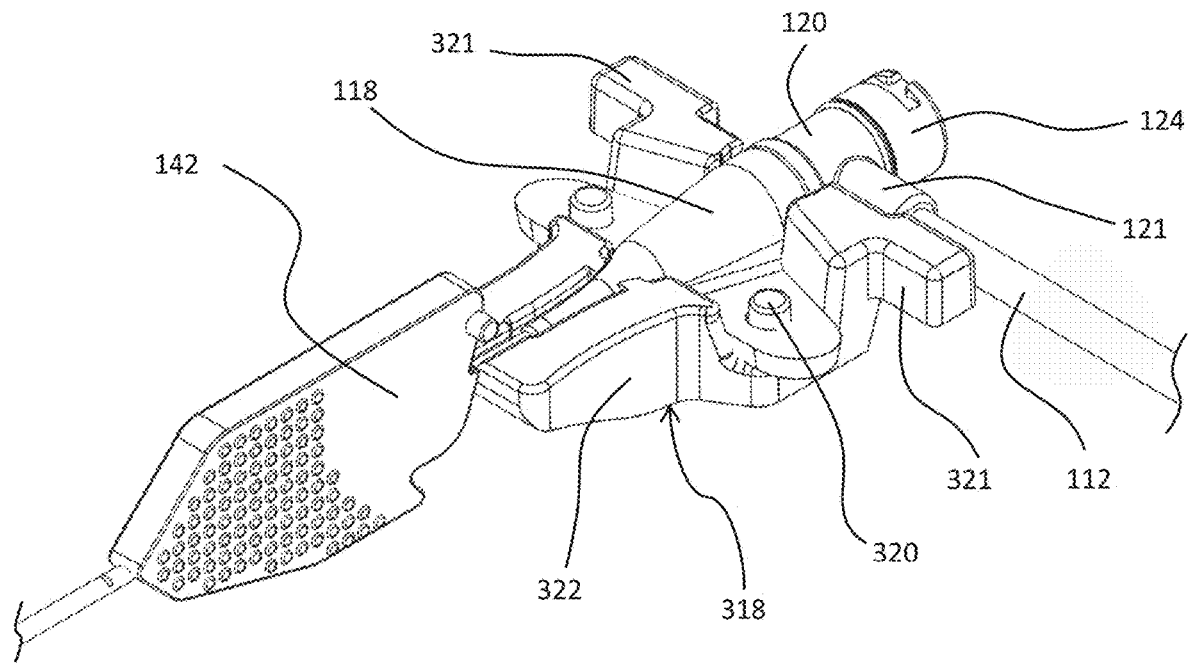
FIG. 4B illustrates a top perspective view of the catheter advancer base, the needle support, and the assembled catheter group.

Referring to FIG. 4A, the catheter advancer base 318 and the needle support 142 are shown isolated from the rest of the catheter insertion device 100. FIG. 4B shows the catheter group 102 engaged with the catheter advancer base 318 and the needle support. An upper surface of the catheter advancer base 318 includes a catheter seat 319 configured to matingly receive the catheter hub 118. In one implementation, the retaining member 323 may be configured to allow the catheter hub 118 to securely snap into the catheter seat 319. A pair of spaced apart fasteners, such as pins 320, are provided within the catheter seat 319 for connecting to respective connector holes on each wing section, which extend outwardly on opposing sides of the catheter hub 118. The catheter hub 118 stays connected to and moves with the catheter advancer base 318 when the catheter advancer base is advanced distally during the catheter insertion procedure, as will be discussed in detail below.

The catheter advancer base 318 may be disconnected and removed from the catheter hub 118 during dressing of the catheter 106 to a patient. The catheter advancer base 318 is also configured to stay with the catheter 106 during advancement and may disconnected therefrom during dressing. A longitudinal slide groove 324 provided on the bottom surface of the catheter advancer base 318 defines a guide track that is configured to slidingly engage the bottom arm 129 of the housing. This guide track is configured to create a sliding motion of the catheter advancer base 318 along the bottom arm 129 and also prevent twisting of the catheter advancer base 318 and catheter hub 118 about their longitudinal axis during such sliding motion when they are advanced forward during catheter insertion. Accordingly, the guide track is configured prevent torsion of the catheter advancer base 318, and thus also prevent torsion of the catheter group 102 and its associated components, when the catheter advancer base rides on the bottom arm 129 of the handle during catheter insertion.

A grip arm 321 is provided on each side of the catheter advancer base 318, and a grip recess 322 is also provided on each side of the catheter advancer base 318. The grip arms 321 and grip recesses 322 allow for alternate grip positions of the catheter advancer base 318 by a practitioner, including a choked up hand grip position. For instance, in such a choked up hand position, the user may grip the catheter insertion device 100 using one hand by placing a thumb in the grip recess 322 located on a first side of the catheter advancer base 318, and a middle finger in the grip recess 322 located on an opposite second side of the catheter advancer base 318. The user's index finger may then be curled up so that it can manipulate the slider 138. In this choked up hand position, the closer a user's hand is located toward the distal end of the handle allows for improved control of gripping and advancing the catheter advancer base 318 during operation. The catheter advancer base 318 may be symmetric about its longitudinal axis to allow for both right-handed and left-handed placement by a user.

Figure 5A:
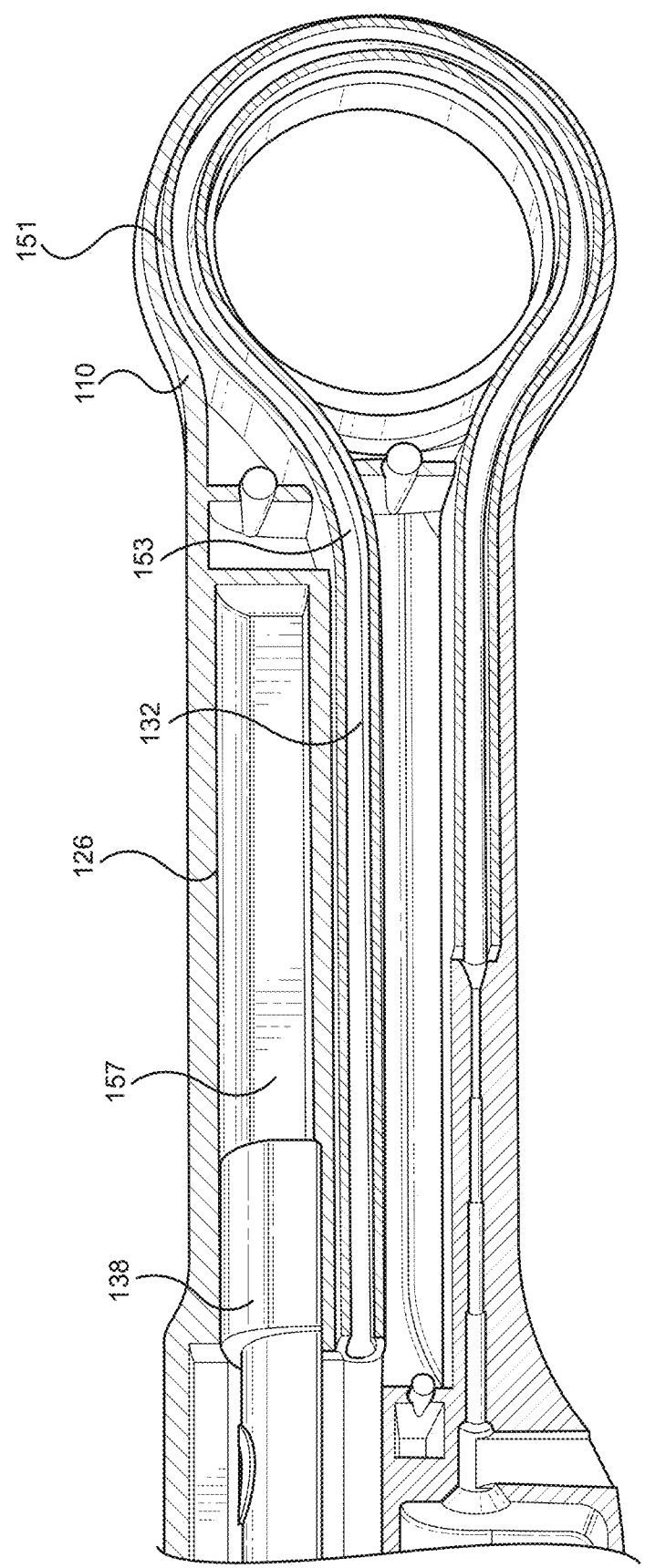
FIG. 5A illustrates a cross-sectional side view of a right housing of an assembled catheter insertion device.

Referring to FIG. 5A, a cross-sectional side view of the right housing 126 including the slider 138 and the guidewire 132 is illustrated. The handle 110 includes a looped proximal end 151 through which the guidewire 132 passes. In particular, the guidewire 132 passes through the channel 153 defined by the handle 110. The diameter of the channel 153 is slightly greater than the diameter of the guidewire 132 so that the guidewire 132 stably passes through the channel 153. The slider 138 can be slid by a finger, such as the index finger in overhand operation or the thumb in underhand operation, of a practitioner proximally and distally within a chamber 157 defined by the handle 110. The chamber 157 is sized to be slightly larger than the slider 138 to stabilize the movement of the slider 138 within the chamber 157.

Due to the looping of the guidewire 132 within the looped proximal end 151, proximal movement of the slider 138 translates into distal movement of the distal tip of the guidewire 132 and vice versa. The looping of the guidewire 132, as opposed to a linear geometry, also enables one-handed operation of the catheter insertion device 100 while maintaining continuous grip of the gripping features 148 of the handle 110. In addition, the looping of the guidewire 132 reduces the likelihood of piercing the vasculature of the patient during advancement of the guidewire 132 due to the force of the practitioner being indirectly applied to the guidewire 132.

Figure 5B:
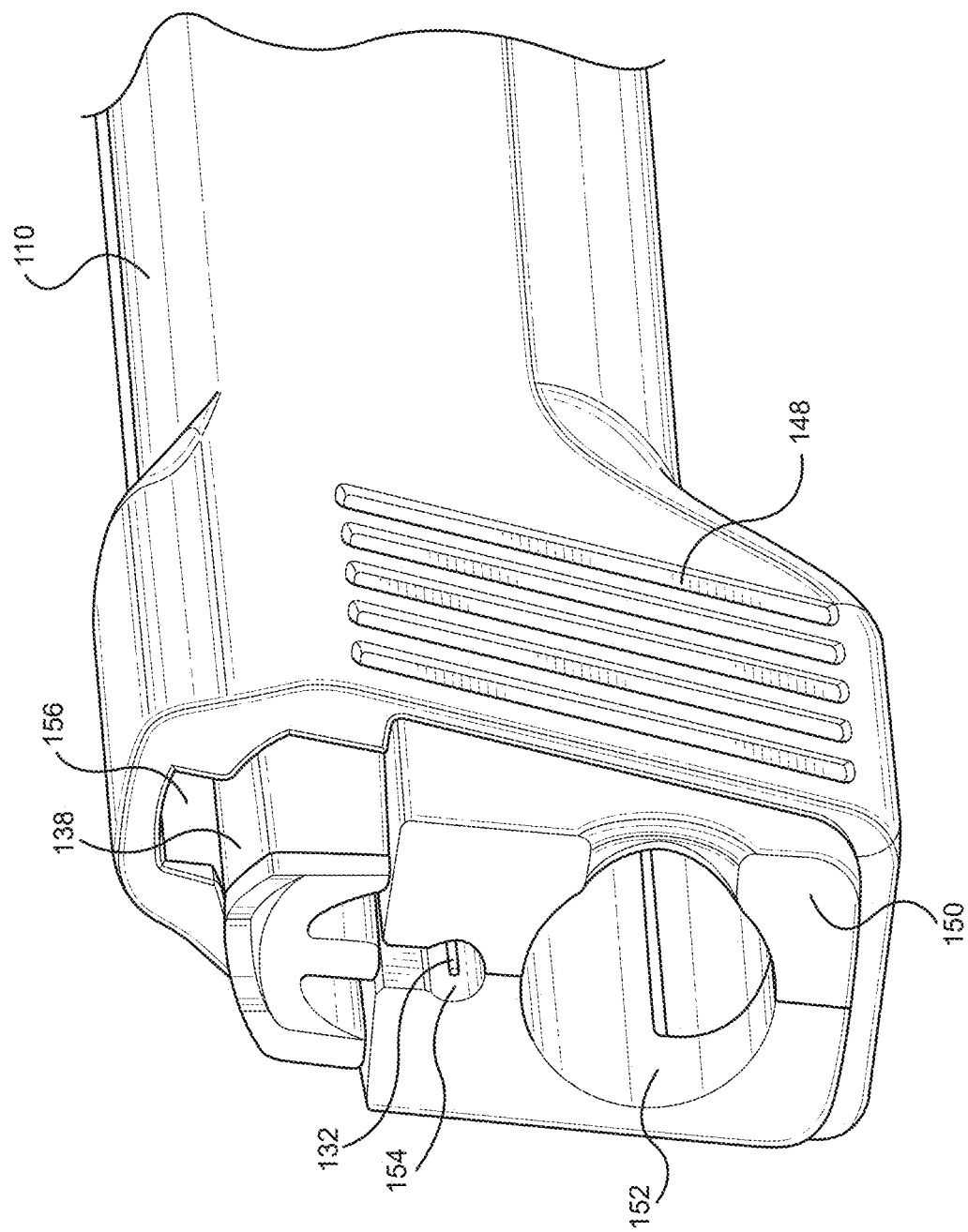
FIG. 5B illustrates a cross-sectional view of a handle of an assembled catheter insertion device.

Referring to FIG. 5B, a cross-section view of the assembled handle 110 with the guidewire 132 and the slider 138 is illustrated. The handle 110 includes gripping features 148 that help the practitioner grip the handle 110 of the catheter insertion device 100. A right-handed practitioner can, for example, grip the gripping feature 148 on the left housing 128 using his thumb and grip the gripping feature 148 on the right housing using his middle finger. Alternatively, a left-handed practitioner can, for example, grip the gripping feature 148 on the left housing 128 using his middle finger and grip the gripping feature 148 on the right housing using his thumb. The handle 110 can be gripped by the practitioner overhand or underhand using the same fingers. The gripping feature 148 may comprise a plurality of depressed lines, grooves, corrugations, projections, or a roughened surface, among others, formed on the outer surface of the handle 110. For example, raised lines may be formed in place of the depressed lines, a textured surface may be formed, a plurality of bumps may be formed, or a different material, such as rubber, may be provided over the region of the handle 110 corresponding to the gripping features 148.

Three openings are defined by the front face 150 of the handle 110. The bottom opening 152 is sized to receive the rigid hub cap 124 of the catheter group 102. In particular, the diameter of the bottom opening 152 is slightly greater than the diameter of the rigid hub cap 124. The middle opening 154 is sized to receive the guidewire 132 and the needle cannula 130, and the top opening 156 is sized to receive the slider 138 and the proximal arm 174 of the release 140. The top opening 156 includes a wider bottom region that receives the slider 138 and a narrower top region that receives the proximal arm 174 of the release 140. The bottom opening 152 and the middle opening 154 are separated by a portion of the handle 110, whereas the middle opening 154 and the top opening 156 are not separated to allow a bottom arm 158 of the slider 138 to slide within middle opening 154, as explained in greater detail below.

Figure 6:
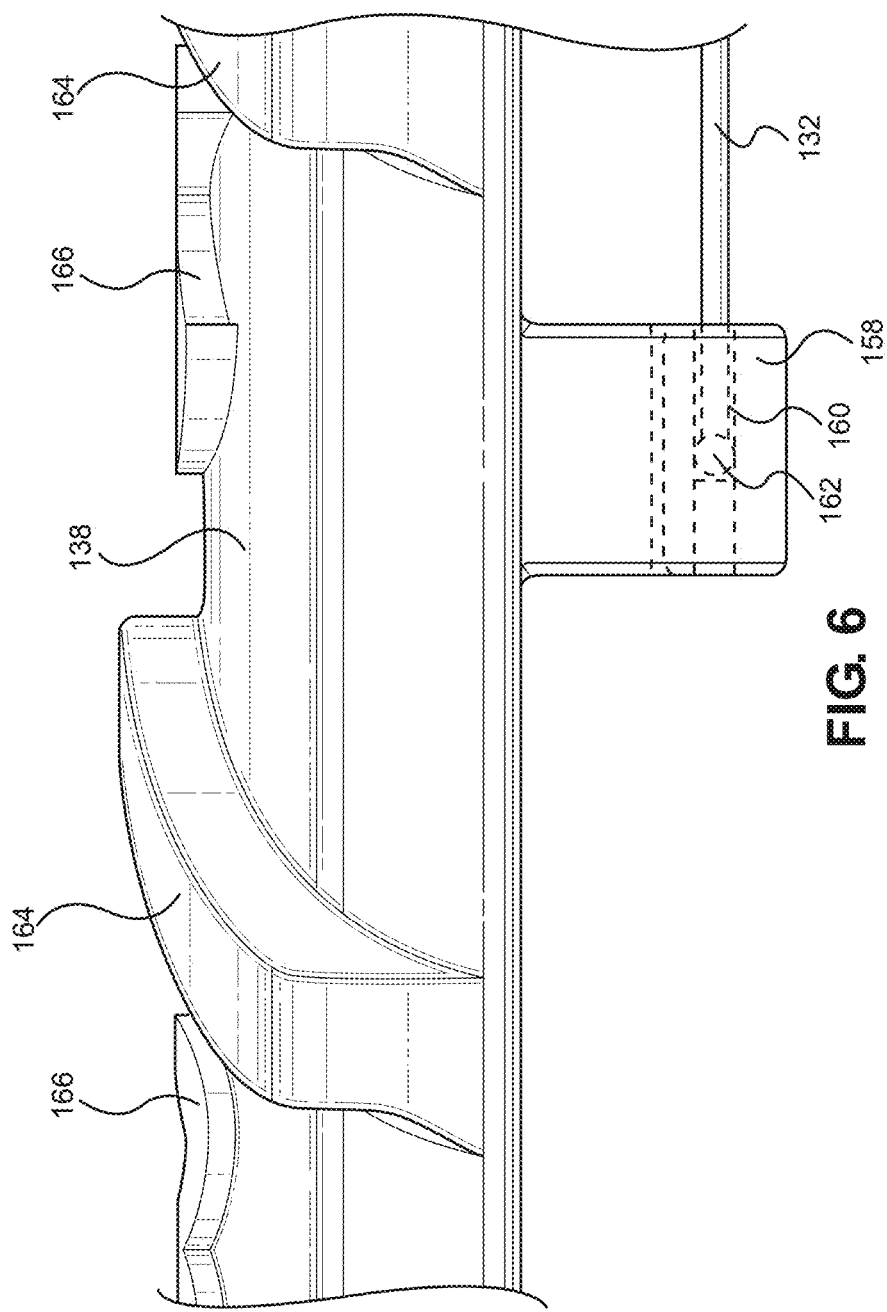
FIG. 6 illustrates a side elevation view of a portion of a slider of the insertion group of the catheter insertion device.

In particular, referring to FIG. 6, a transparent side view of a portion of the slider 138 is illustrated. The slider 138 includes a bottom arm 158 extending from the bottom of the slider 138 in a direction perpendicular to the longitudinal axis of the slider 138. The bottom arm 158 includes a through hole 160 that receives the proximal end 133 of the guidewire 132. The proximal end 133 may include a ball 162 to anchor the tip of the proximal end of the guidewire 132 in place. The through hole 160 has an internal diameter that is slightly larger than the outer diameter of the guidewire 132 but slightly smaller than the diameter of the ball 162 formed at the tip end of the guidewire 132. The guidewire 132 is therefore secured within the through hole 160 by an interference fit. The through hole 160 does not extend along the entirety of the length of the bottom arm 158, such that the distal end of the through hole 160 is closed. Although the ball 162 is secured within the through hole 160 by an interference fit, in some implementations, the ball 162 may be secured by an adhesive, by a threaded connection, or the like.

Due to the interference fit between the through hole 160 and the guidewire 132, as the slider 138 is moved in a longitudinal direction for a given distance, the guidewire will also move in the opposite direction for the same distance and vice versa. Stated another way, the portion of the guidewire 132 that is between the slider 138 and the loop portion in the handle will move in the same direction as the slider itself. Conversely, the portion of the guidewire 132 that is between the loop portion of the handle and the distal tip will move in the opposite direction of the slider 138. The slider 138 includes one or more grips 164 that allow a finger, such as the index finger in an overhand operation or the thumb in an underhand operation, of the practitioner to predictably actuate the slider 138 in either a distal or proximal direction. In some implementations, the grips 164 may be shaped like arrows that point in the proximal direction. Adjacent to each grip 164 may be an indicator 166, such as a number, that indicates a relative extension of the guidewire 132 distally from the sharp needle tip 131.

The guidewire 132 may further comprise a variable stiffness that facilitates insertion of the catheter 106 into the vasculature of a patient. In one implementation, the guidewire 132 may comprise various segments, such as a first segment defining a thin section of increased flexibility, a second segment defining a tapered transitioned section, and a third segment defining a thick and rigid section that assists the catheter 106 in following bends in the guidewire 132. The third segment, which is nearest to the catheter 106 when the variable stiffness guidewire is fully extended, has the most stiffness which helps the catheter more easily follow any bends of the guidewire during insertion into a patient's vasculature. The stiffness gradually decreases towards the distal tip of the guidewire, such that the first segment is the most flexible region since it has the smallest diameter, which may be, for example, between 0.005 in and 0.006 in. The increased flexibility of the first segment allows it to easily bend upon entry into the vasculature in order to minimize piercing through the vasculature wall. As previously noted above, the ball-shaped distal tip of the guidewire 132 also helps minimize such piercing through the vasculature wall. The length of the segment of the guidewire may vary. In one implementation, for example, the length of the first and third segments may be approximately 1.5 cm, and the length of the second segment may be approximately 1.0 cm.

Figure 7A:
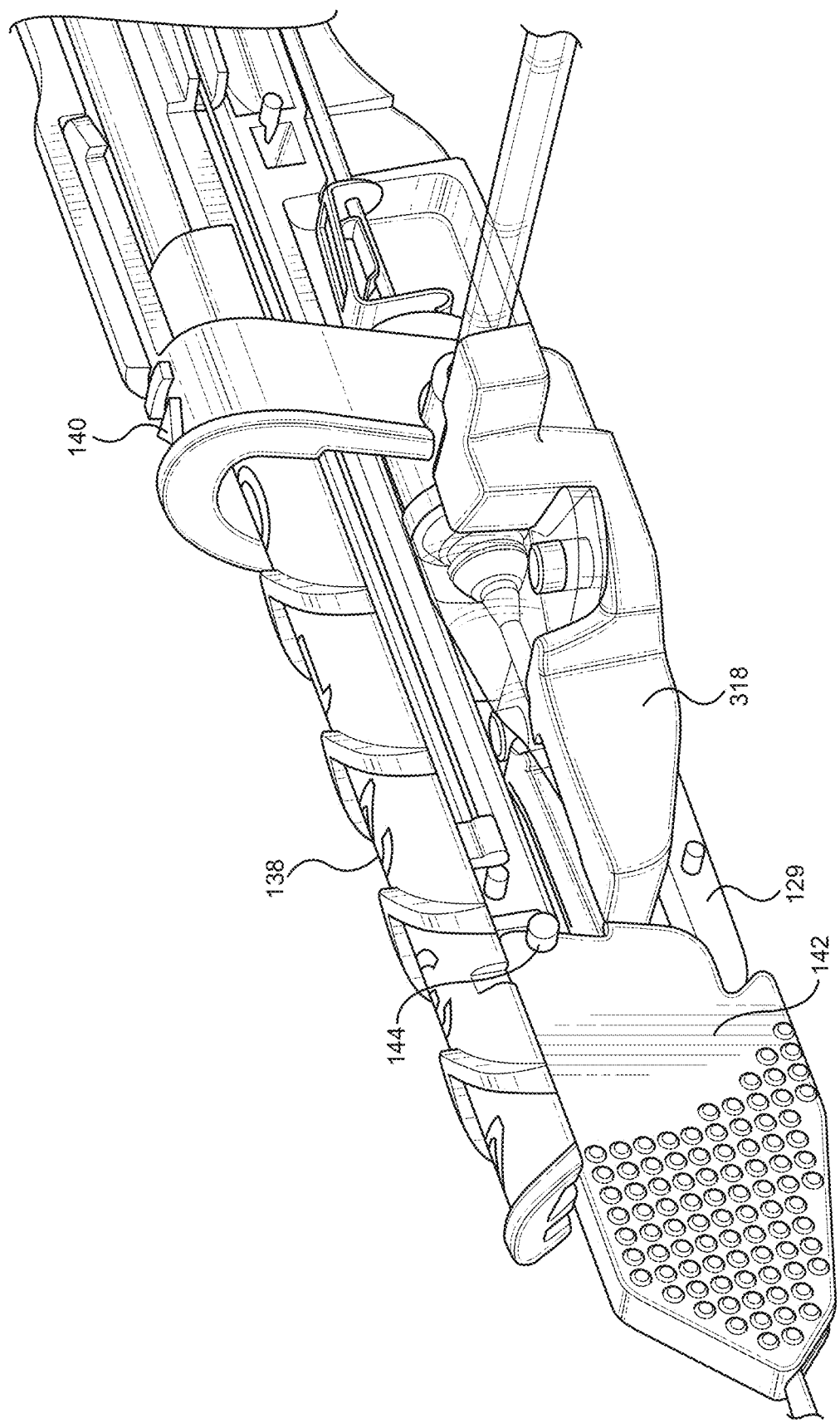
FIG. 7A illustrates a release of the insertion group of the catheter insertion device and a catheter advancer base, as well as a partial cut-away view of a handle of the catheter insertion device.
Figure 7B:
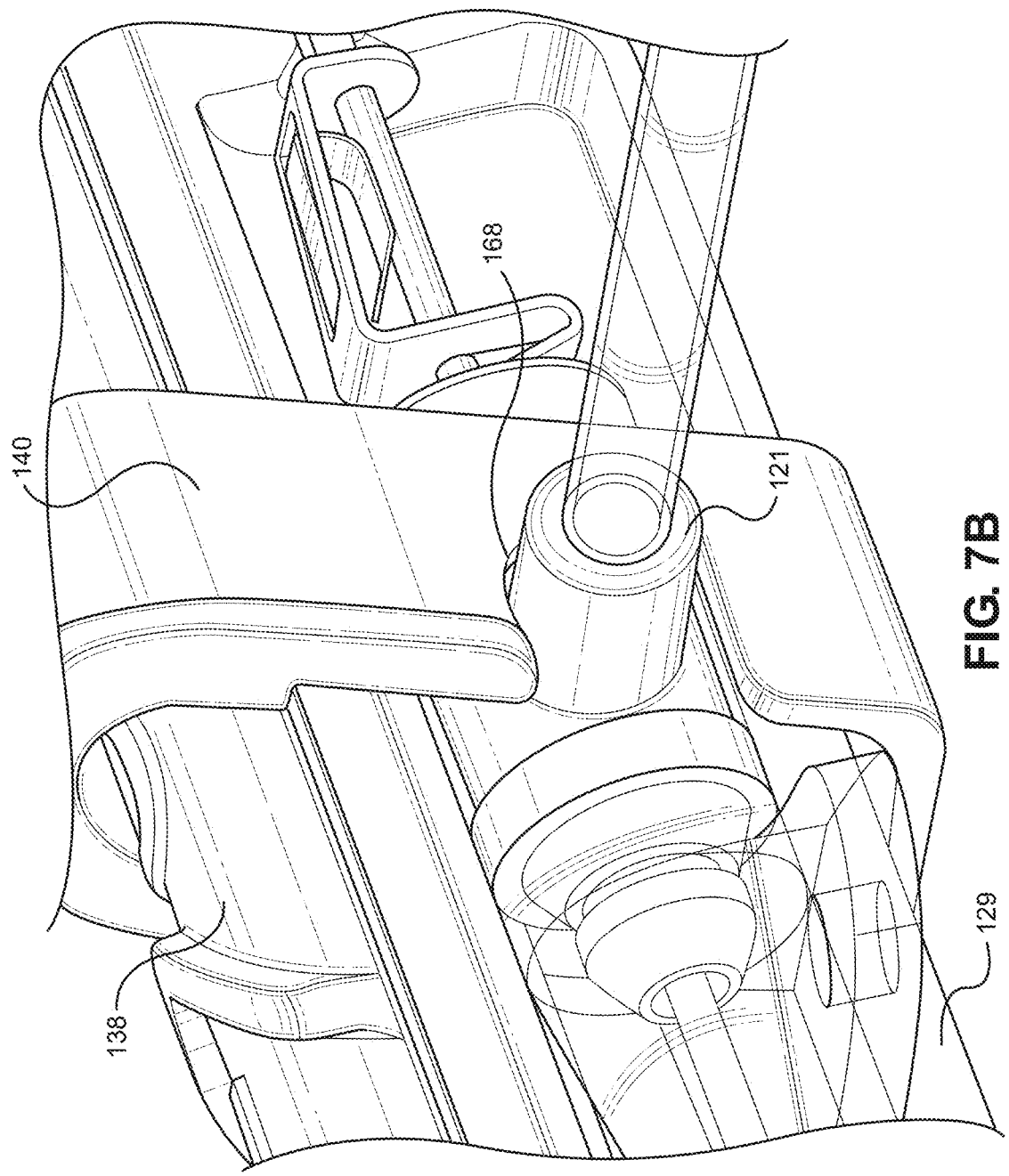
FIG. 7B illustrates an enlarged view of the release of the insertion group of the catheter insertion device without the catheter advancer base.

FIG. 7A shows a portion of the catheter insertion device depicting the release 140 and the catheter advancer base 318, and FIG. 7B shows a portion of the catheter insertion device depicting the release 140 without the catheter advancer base 318. The distal side of the release 140 includes a notch 168 configured to receive the side port 121 of the rigid hub 120. The release 140 is sized to be received from around the bottom arm 129 to the slider 138. The notch 168 is sized to be slightly larger than the diameter of the side port 121 to stably secure the side port 121. When the practitioner actuates the release 140 in a distal direction using, for example, his index finger, the catheter group 102 is also actuated in the distal direction by the same distance through the interface between the notch 168 and the side port 121.

Figure 7C:
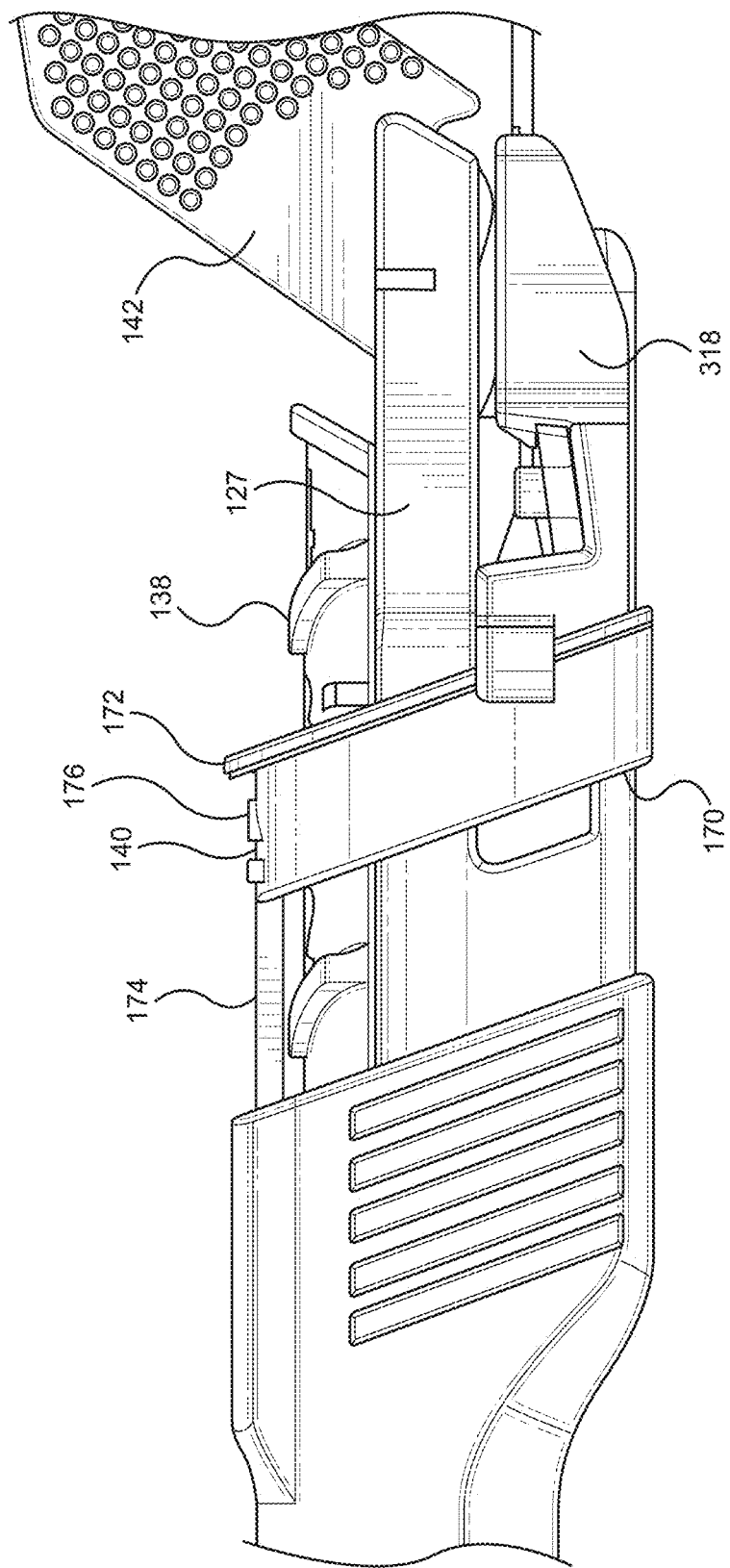
FIG. 7C illustrates a side view of the release in an extended position.

As shown in FIG. 7C, the release 140 includes a continuous side wall 170. If the practitioner's finger were to push down onto the slider 138 or top arm 127 of the handle 110 while the needle cannula 130 is still in the vasculature of the patient, the resulting downward movement of the needle cannula 130 may cause damage to the vasculature of the patient. As such, the release 140 includes a distal lip 172 that extends radially outward from the release 140 in order to help prevent the practitioner's finger from slipping past the distal end of the release 140.

The release 140 also includes a proximal arm 174 having an enlarged proximal end 141. The proximal arm 174 slides within the top opening 156 of the handle 110. The enlarged proximal end of the release 140 is dimensioned to be larger than the top opening 156 so that distal movement of the release 140 is limited to the length of the proximal arm 174, and so that the release 140 does not separate from the handle 110. The release 140 may also include a grip 176 that allows a finger, such as the index finger in an overhand operation or the thumb in an underhand operation, of the practitioner to predictably actuate the release 140 in either a distal or proximal direction.

Figure 8A:
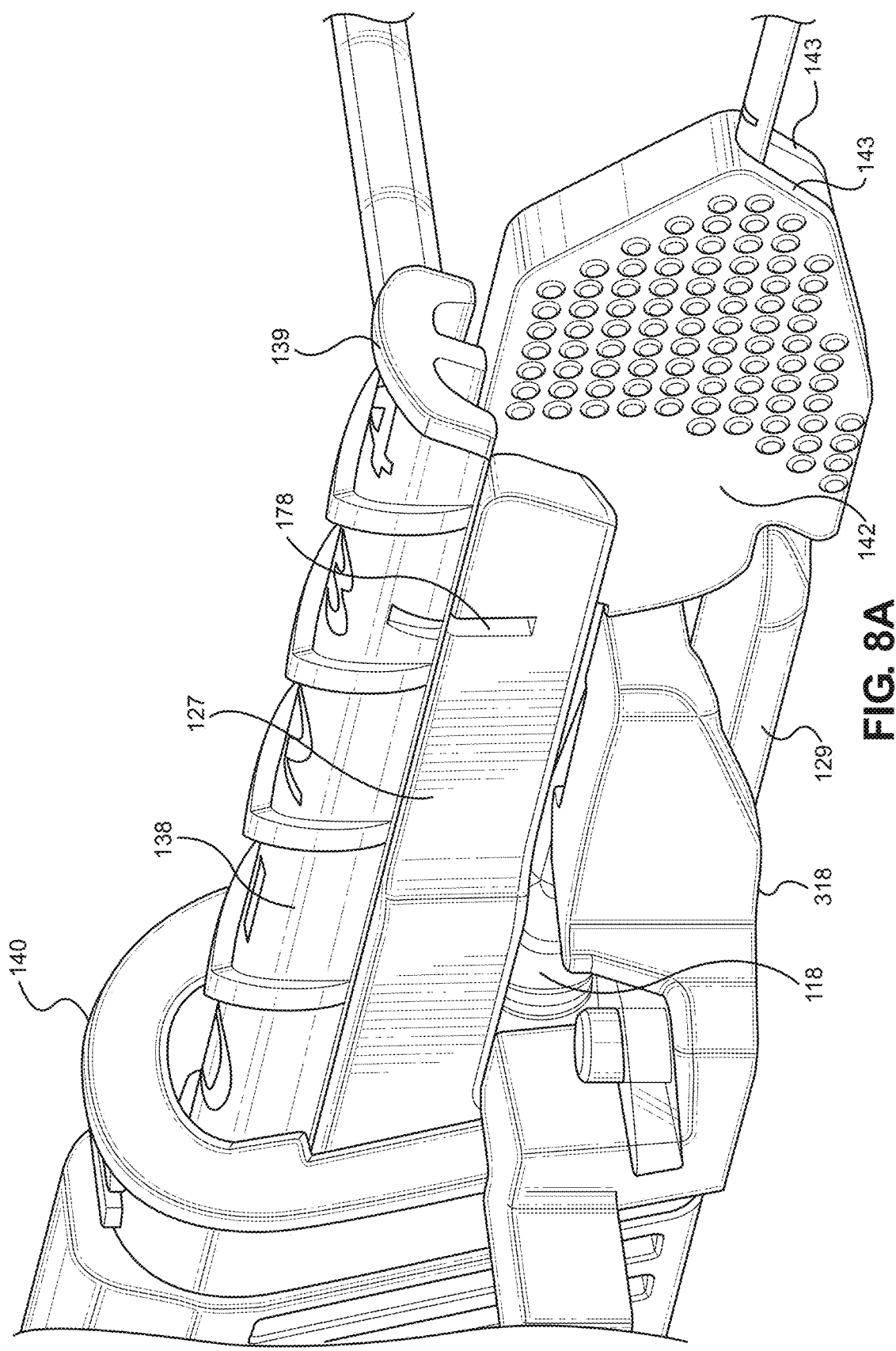
FIG. 8A illustrates a perspective view of a region of the assembled catheter insertion device having the slider in a fully extended position and the release in a fully retracted position.

Referring to FIG. 8A, a partially transparent perspective view of a region of the assembled catheter insertion device 100 is illustrated. The bottom arms 129 of the right housing 126 and the left housing 128 abut against one another to support the weight of the catheter hub 118. The top arms 127 of the right housing 126 and the left housing 128 are spaced apart by a distance slightly greater than the width of the needle support 142 to allow the needle support 142 to swing upwards during removal of the catheter group 102. The outer surface of each opposite spaced apart parallel wall 143 of the needle support 142 includes a pivot member 144, such as a hinge, pivotally connected to the corresponding inner surface of each spaced apart top arm 127 of the handle.

The needle support 142 includes two parallel walls 143 that are perpendicular to the plane of the top surface of the bottom arms 129. As explained above, the parallel walls 143 are spaced apart by a distance slightly greater than the outer diameter of the elongated catheter 106 to stabilize the needle cannula 130 during insertion into the vasculature of the patient. In various implementations, the parallel walls 143 of the needle support 142 may be sized to mate with the catheter or needle gauge size, such as 18 ga, 20 ga, or 22 ga, among others. Both top arms 127 also include a groove 178 configured to receive a corresponding tongue of the needle guard 137. Such a tongue and groove connection stably secures the needle guard 137 to the handle 110 to protect the catheter before use of the catheter insertion device 100.

Figure 8B:
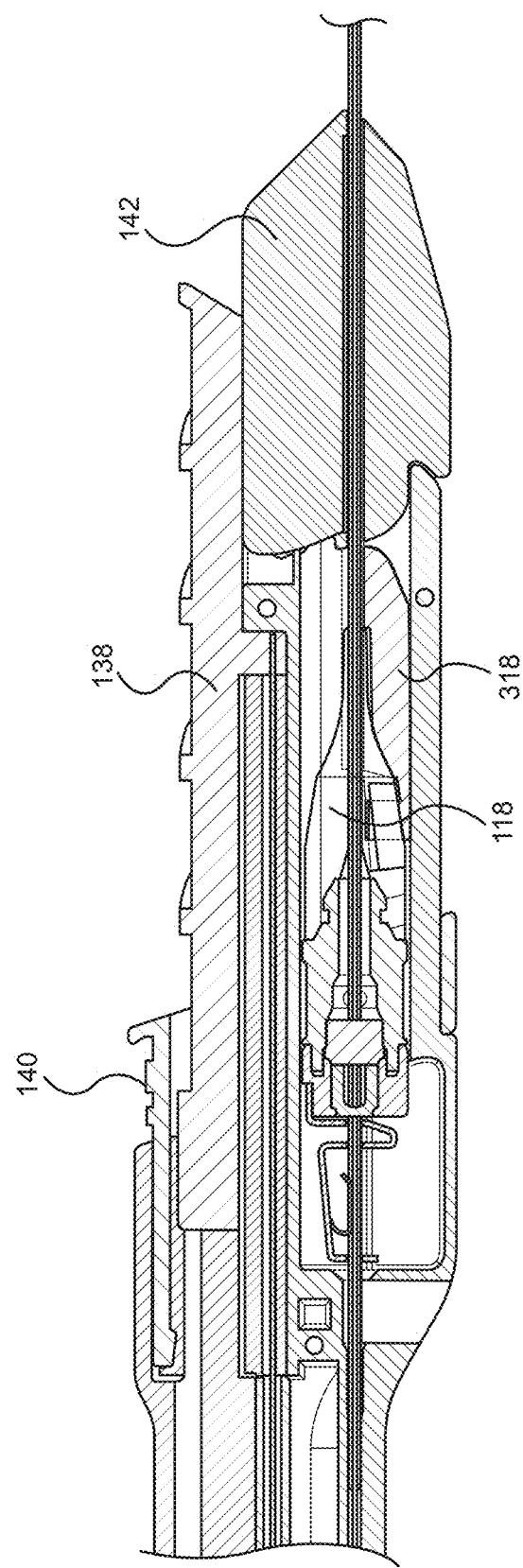
FIG. 8B illustrates a cross-sectional side view of a region of the catheter insertion device along the center longitudinal plane of the handle in a pre-advanced position of the catheter group.
Figure 8C:
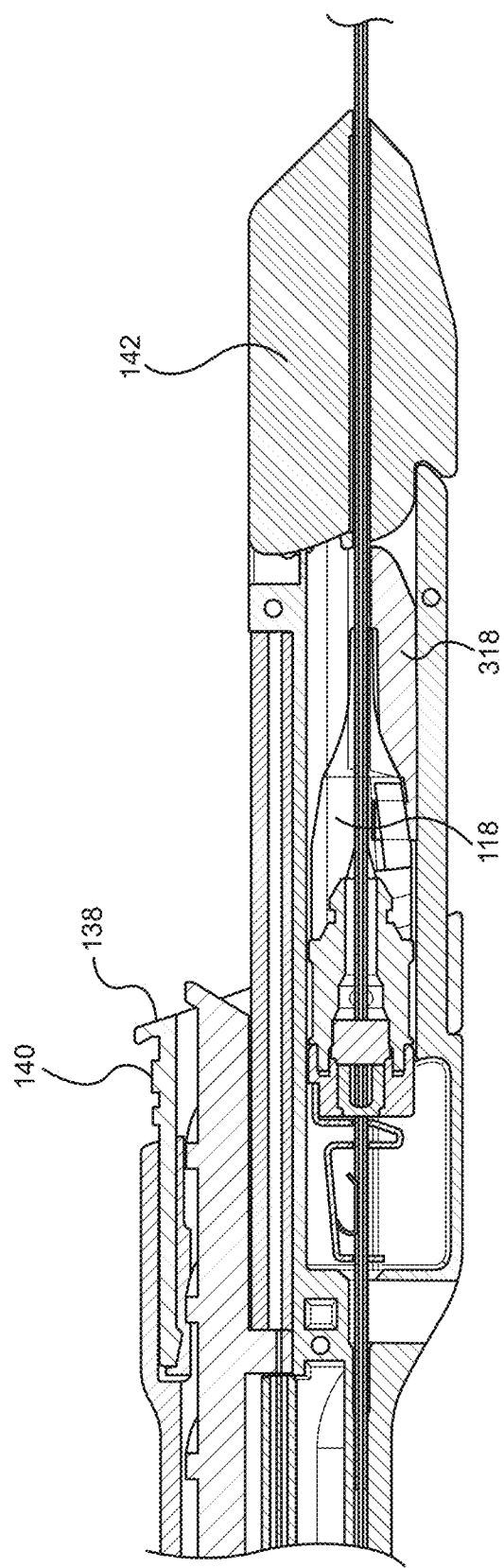
FIG. 8C illustrates a cross-sectional side view of the region of the catheter insertion device along the center longitudinal plane of the handle following actuation of the slider by the practitioner.
Figure 8D:
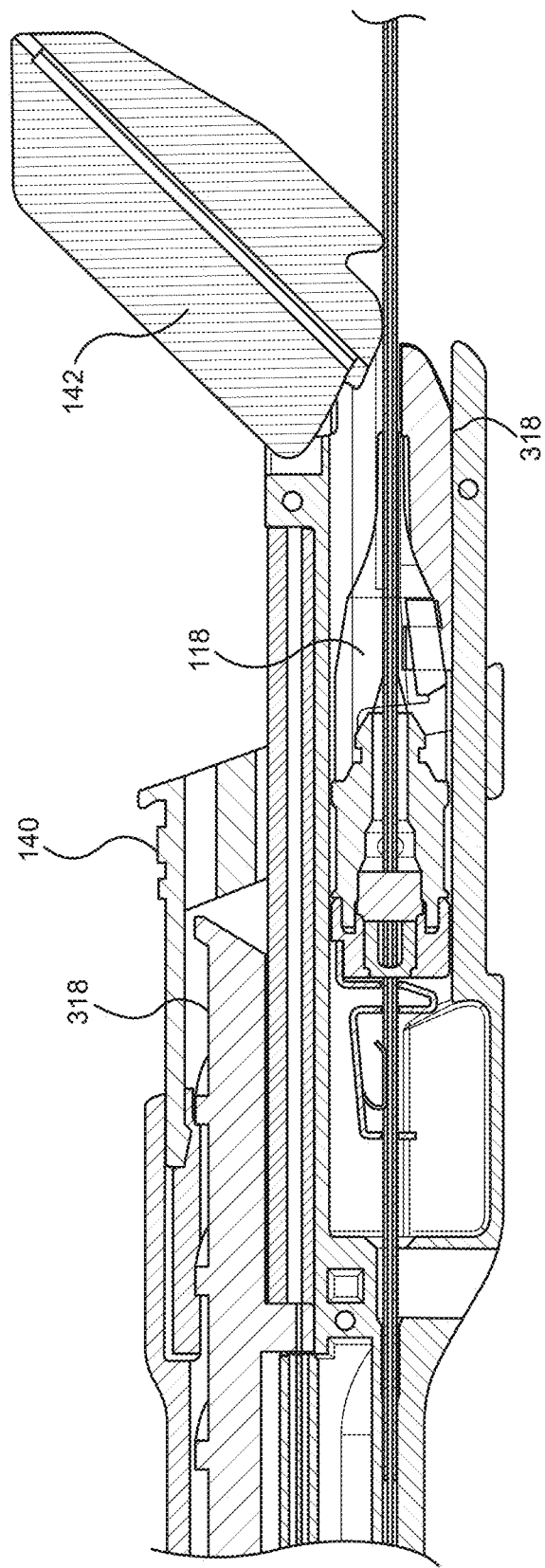
FIG. 8D illustrates a cross-sectional side view of the region of the catheter insertion device along the center longitudinal plane of the handle following actuation of the release by the practitioner.
Figure 8E:
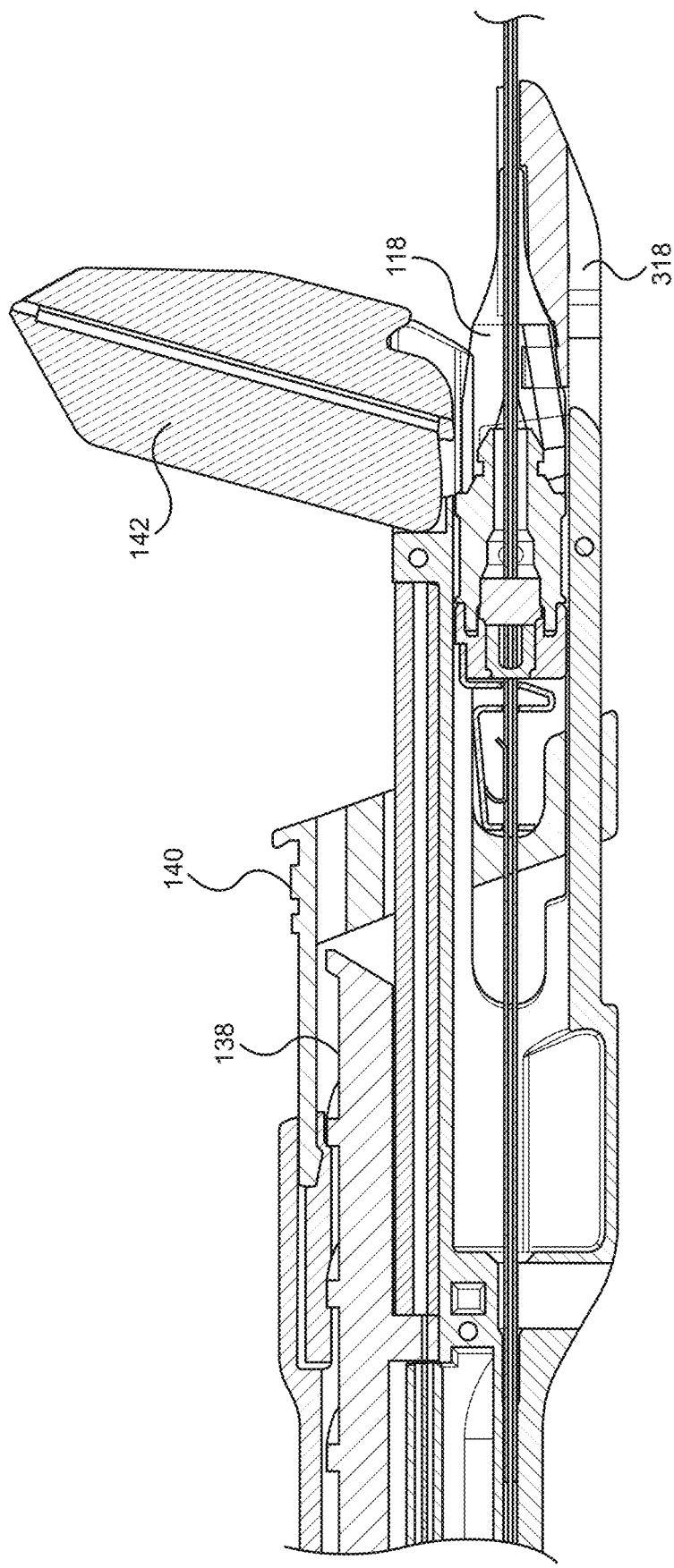
FIG. 8E illustrates a cross-sectional side view of the region of the catheter insertion device along the center longitudinal plane of the handle following further advancement of the catheter group along the handle by the practitioner.
Figure 8F:
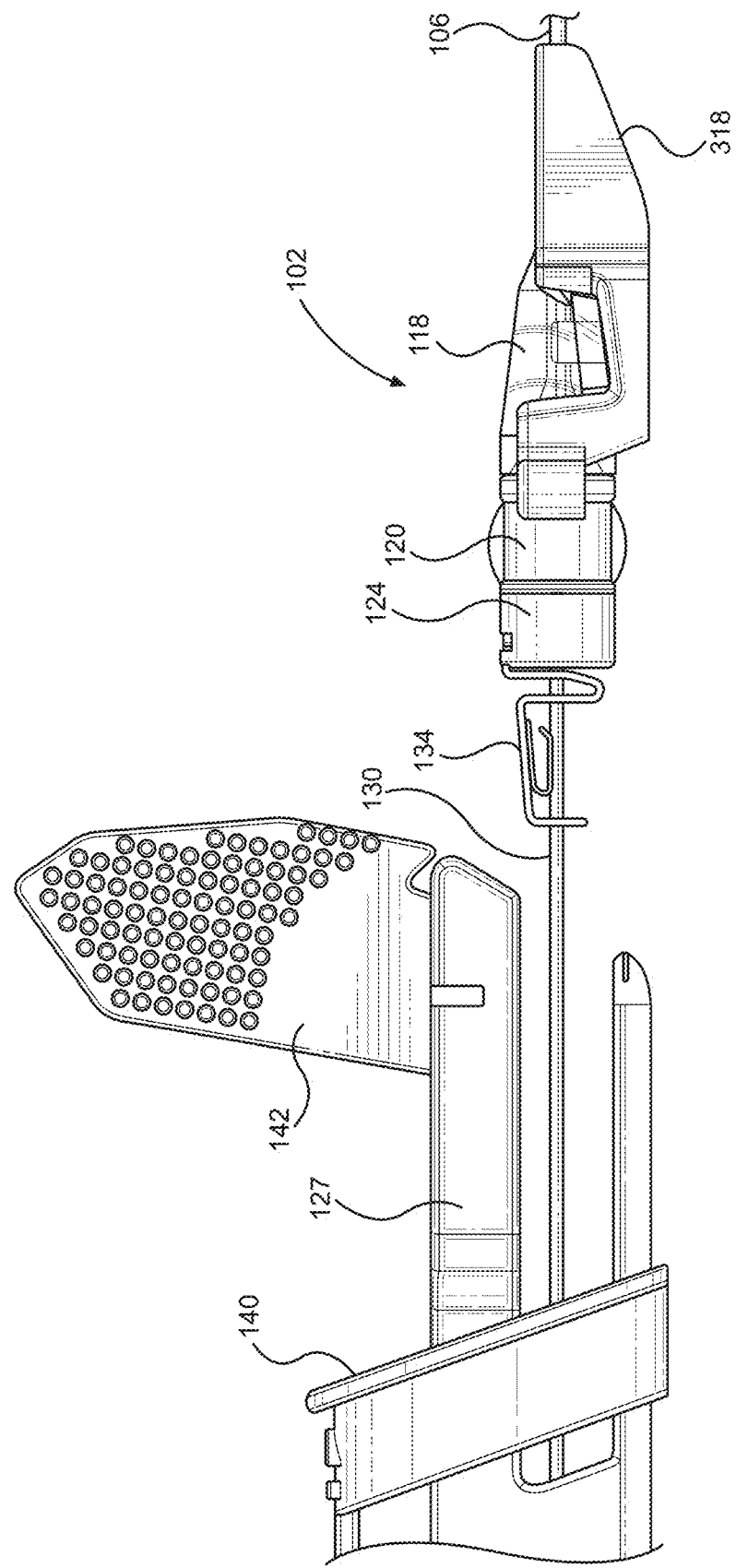
FIG. 8F illustrates a side view of the region of the catheter insertion device following advancement of the catheter group from the handle by the practitioner.

FIGS. 8A-8F illustrate various operating positions of the catheter insertion device 100 during advancement of the catheter group 102 from the insertion group 104. When the slider 138 is in the fully extended position, as shown in FIG. 8B, the top portion 147 of the needle support 142 abuts the bottom surface of the slider 138 to block the needle support 142 from swinging upward which in turn blocks the catheter advancer base 318 from moving, thus locking the release 140 from being actuated in order to retain the catheter group 102 in place between the needle support 142 and the release 140. Upon sliding the slider 138 proximally toward the handle 110, as will be discussed below, the top surface 147 of the needle support 142 becomes free since it no longer abuts the bottom surface of the slider. Further, the release 140 becomes unlocked such that pushing it distally toward the needle support 142 urges the catheter advancer base 318 distally into contact with the needle support 142. The catheter advancer base 318 accordingly urges the needle support 142 to swing upward about the pivot member 144, thus creating a clearance for the entire catheter group 102 to be disconnected from the insertion group 104, as shown in FIG. 8F, so that the catheter 106 can be advanced forward into the patient's vasculature.

Before the practitioner slides the slider 138 proximally, the distal end 139 of the slider 138 extends beyond the distal end of the top arm 127 and, as such, extends distally along a portion of the needle support 142 without extending beyond the needle support. As shown in FIG. 8B, which illustrates a cross-sectional view of the region of the assembled catheter insertion device 100 along the center longitudinal plane of the handle 110, the needle support is oriented in a support position such that the bottom surface of the slider 138 abuts against the top portion 147 of the needle support 142 before the slider 138 is slid proximally in order to prevent the needle support 142 from swinging out of engagement with the catheter prior to being inserted in the vasculature of the patient.

In this support position, or pre-advancement position, the needle support 142 blocks the catheter advancer base 318 and the catheter group 102 from moving forward. A portion of the catheter 106 proximate to the distal end of the needle support 142 is supported to resist force from three directions such as from the bottom, the left side, and the right side. A portion of the catheter 106 proximate to the proximal end of the needle support 142 is supported by the rigid catheter advancer base 318 to resist force from a fourth direction, such as from the top. The needle support 142 thus provides sufficient support to the catheter 106 in order to improve its rigidity in order to avoid excessive bending during insertion into the vasculature of a patient. A lip 149 is provided on the bottom of the needle support 142 and is configured to hood around a distal end of the bottoms arms 129 of the handle in order to prevent the catheter group 102 from popping out accidentally during use. Further, when the needle support 142 is oriented in the support position, the catheter advancer base 318 and the catheter hub 118 remain nested between the top and bottom arms 127, 129 of the housing 110, and between the release 140 and the needle support 142 to retain the catheter group 102 during use.

FIG. 8C illustrates a cross-sectional view of the region of the assembled catheter insertion device 100 along the center longitudinal plane of the handle 110 following actuation of the slider 138 by the practitioner. The distal end 139 of the slider 138 is slid proximal of the needle support 142 so that the top portion 147 no longer abuts the bottom surface of the slider 138 and is free to swing upwards as the catheter group 102 is separated from the insertion group 104.

FIG. 8D illustrates a cross-sectional view of the region of the assembled catheter insertion device 100 along the center longitudinal plane of the handle 110 following actuation of the release 140 by the practitioner. According to another aspect, the practitioner may advance the catheter without using the release 140. As shown in FIG. 8D, the release 140 is pushed forward toward the distal end of the handle such that it correspondingly pushes the rigid hub 120 distally so that the catheter advancer base 318 contacts the needle support 142 and urges the needle support 142 to swing upward about the pivot members 144.

The release 140 may be pushed forward until it reaches a stop position, after which the practitioner may continue advancing the catheter group 102 by gripping the catheter advancer base 318 and moving it forward. According to another aspect, the practitioner may grip the extension line 108, or more particularly an arm of the rigid hub that contains the extension line inside of it, to advance the catheter group 102 forward. As previously discussed, a practitioner may grip each grip recess 322 of the catheter advancer base 318 in a choked up hand position in order to facilitate advancement of the catheter advancer base 318. As shown in FIG. 8E, the needle support 142 continues to swing out of the way of the catheter advancer base 318 and catheter hub 118 during advancement thereof. The needle support 142 is therefore moved out of the path of the catheter advancer base 318 and the catheter hub 118 in order to allow the distal end of the catheter advancer base 318 and the catheter hub 118 to extend distally beyond the needle support 142. The catheter advancer base 318 and the catheter hub 118 thus initially abut the needle support 142, and distally move past the needle support 142 once the needle support 142 is urged by the catheter advancer base 318 to swing upward to provide clearance for full deployment of the catheter group 102, as shown in FIG. 8F. Thus, the catheter group is advanced distally such that the catheter group 102 is distal of the distal end of the handle 110. At this point, the needle safety clip 134 is still mounted to the rigid hub cap 124, as explained below.

Figure 9A:
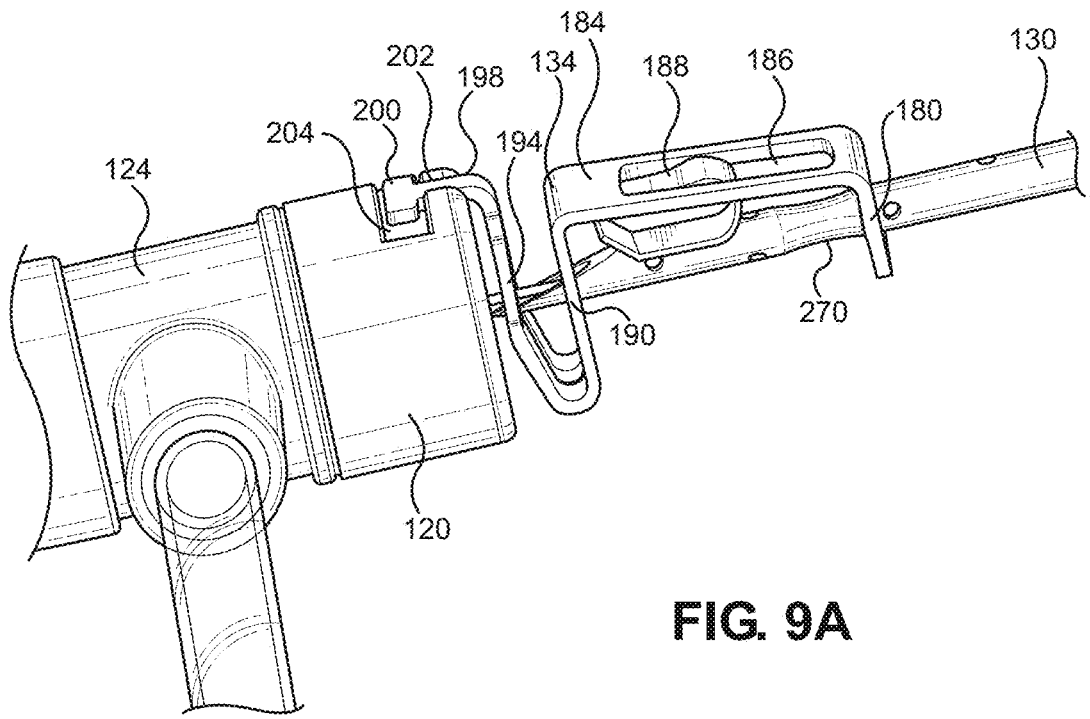
FIG. 9A illustrates a perspective view of a needle safety clip mounted to a catheter hub of the catheter group of the catheter insertion device.
Figure 9D:
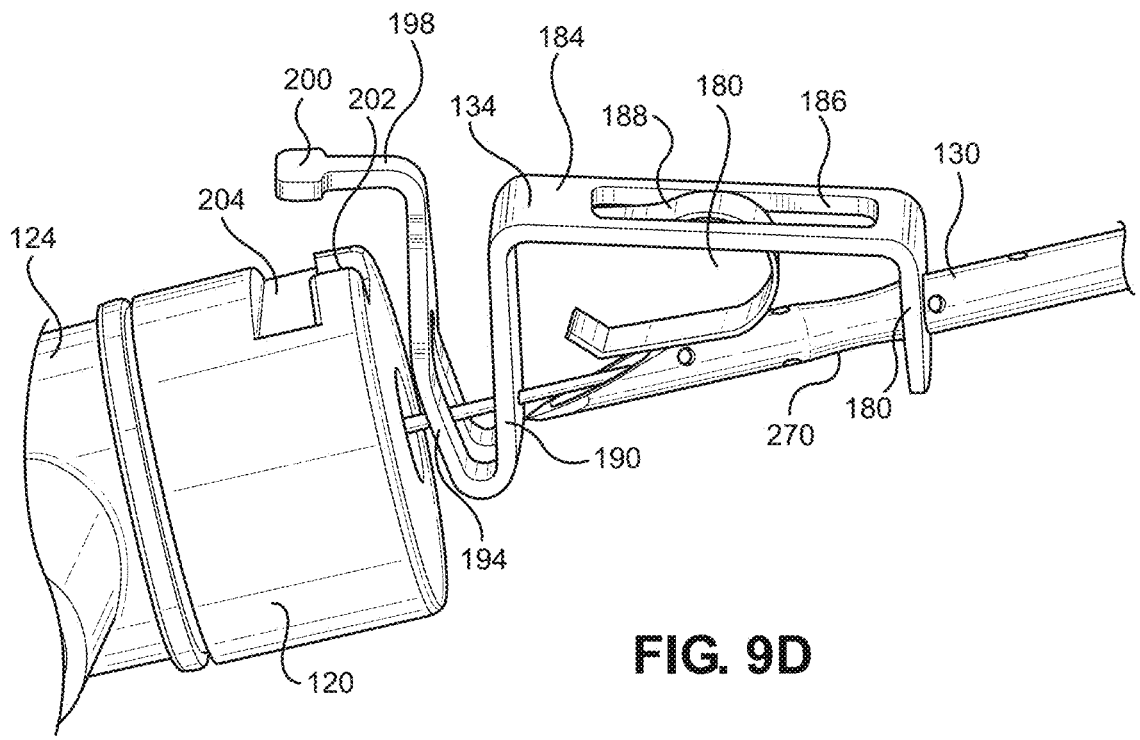
FIG. 9D illustrates an enlarged perspective view of the needle safety clip released from the catheter hub of the catheter group of the catheter insertion device.
Figure 9B:
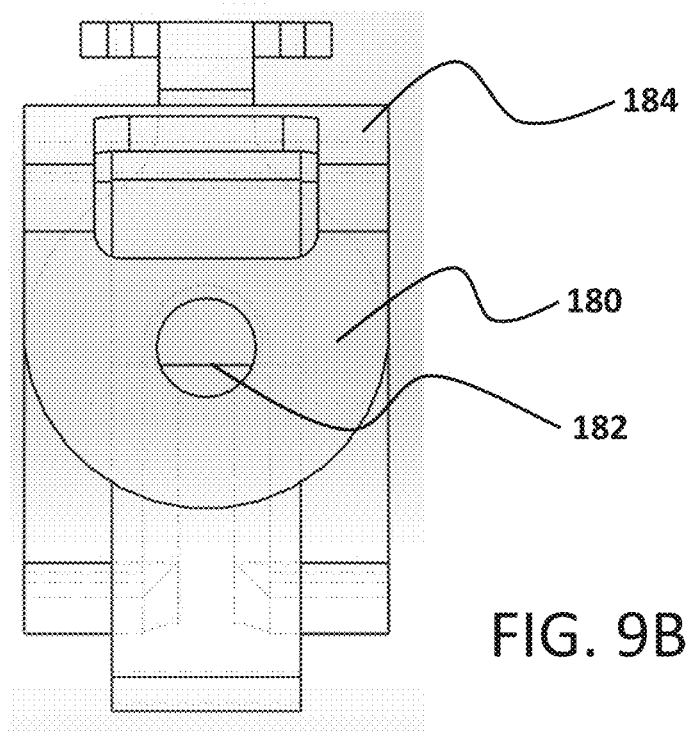
FIG. 9B illustrates a rear view of the needle safety clip.
Figure 9C:
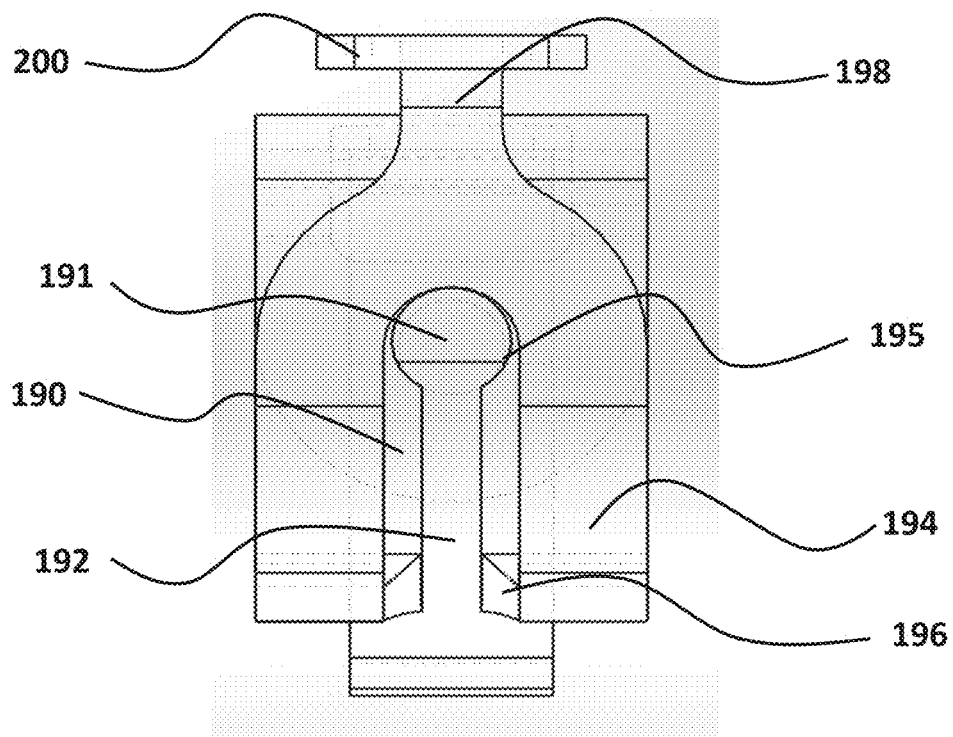
FIG. 9C illustrates a front view of the needle safety clip.

Referring to FIG. 9A, a perspective view of the needle safety clip 134 mounted to the rigid hub 120 is illustrated. Referring to FIG. 9B, a rear view of the needle safety clip 134 is illustrated. Referring to FIG. 9C, a front view of the needle safety clip 134 is illustrated. The needle safety clip 134 includes a proximal wall 180 that includes a round aperture 182 having a diameter slightly greater than the outer diameter of the needle cannula 130. In some implementations, the round aperture 182 may have a sharp inner surface to grip the outer surface of the needle cannula 130 when the needle cannula 130 is at an angle with respect to the central axis of the round aperture 182. In other words, the sharp inner surface of the round aperture 182 digs into the outer surface of the needle cannula 130 when the needle cannula 130 is tilted with respect to the needle safety clip 134, as shown in FIG. 9D, to prevent movement of the needle cannula 130 with respect to the needle safety clip 134.

Referring back to FIG. 9A, a top wall 184 extends distally of the proximal wall 180 and defines a top opening 186. The top opening 186 allows the spring arm 188 to extend partially above the top wall 184 in its compressed state, as shown in FIG. 9A. The spring arm 188 is illustrated having a C-shape. However, the spring arm 188 may be designed to have other shapes that are resilient and may be shaped to be, for example, stepped, blocked, jagged, or amorphous. The top distal portion of the spring arm 188 is connected to the distal bottom surface of the top wall 184 to secure the spring arm 188 to the rest of the needle safety clip 134. The spring arm 188 may be made of any flexible material, such as, for example, plastic, stainless steel, aluminum or titanium. The spring arm 188 may be made of the same material as the rest of the needle safety clip 134 or made of a different material having the desired characteristics.

A first distal wall 190 extends downward from the distal end of the top wall 184 and defines a first distal channel. A second distal wall 194 curves upward from the first distal wall 190 and defines a second distal channel. A narrow tab 198 extends distally from the distal end of the second distal wall 194 and a broad tab 200 extends distally from the narrow tab 198. The narrow tab 198 is received within a narrow recess 202 at the top of the rigid hub cap 124 and the broad tab 200 is received within a broad recess 204 at the top of the rigid hub cap 124 to mount the needle safety clip 134 to the rigid hub cap 124. When the needle safety clip 134 is mounted to the rigid hub cap 124, the narrow tab 198 prevents lateral movement of the needle safety clip 134 while broad tab 200 prevents longitudinal movement of the needle safety clip 134.

Turning back to FIG. 9C, the first distal wall 190 defines a channel having a round top region 191 and a rectangular bottom region 192. The diameter of the round top region 191 is slightly larger than the outer diameter of the needle cannula 130 to allow the needle cannula 130 to slide through the round top region 191 with low friction and to prevent lateral movement of the needle cannula 130. The rectangular bottom region 192 has a width that is less than the outer diameter of the needle cannula 130 to both keep the safety from springing upward until the needle tip is between the first distal wall and the second distal wall and block the needle cannula 130 from being able to extend distally past the second distal wall 194, as explained in greater detail below. The second distal wall 194 also includes a round top region 195 that has a diameter that is greater than the outer diameter of the needle cannula 130 and a rectangular bottom region 196. The width of the rectangular bottom region 196 may be equal to the diameter of the round top region 195 to allow the needle cannula 130 to move downward relative to the needle safety clip 134 under force of the spring arm 188.

Referring to FIG. 9D, a perspective view of the needle safety clip 134 released from the rigid hub 120 is illustrated. After the needle cannula 130 is withdrawn from the rigid hub 120, it passes proximally through the round top region 195 of the second distal wall 194 and then through the round top region 191 of the first distal wall 190. Once the round top region 191 does not stabilize the needle cannula 130 (that is, once the width of the sharp needle tip, $W_n$, becomes smaller than the width of the rectangular bottom region 192), the needle safety clip 134 is free to tilt relative to the needle cannula 130. The spring arm 188 then decompresses, as shown in FIG. 9D, to push the needle safety clip 134 upward. Because the needle cannula 130 is still within the round aperture 182, it is gripped by the sharp inner edges of the round aperture 182, which prevents longitudinal movement of the needle cannula 130 with respect to the needle safety clip 134. As such, the first distal wall 190 and the second distal wall 194 cover the sharp needle tip 131 and protect the practitioner from potential needle pricks.

Figure 9E:
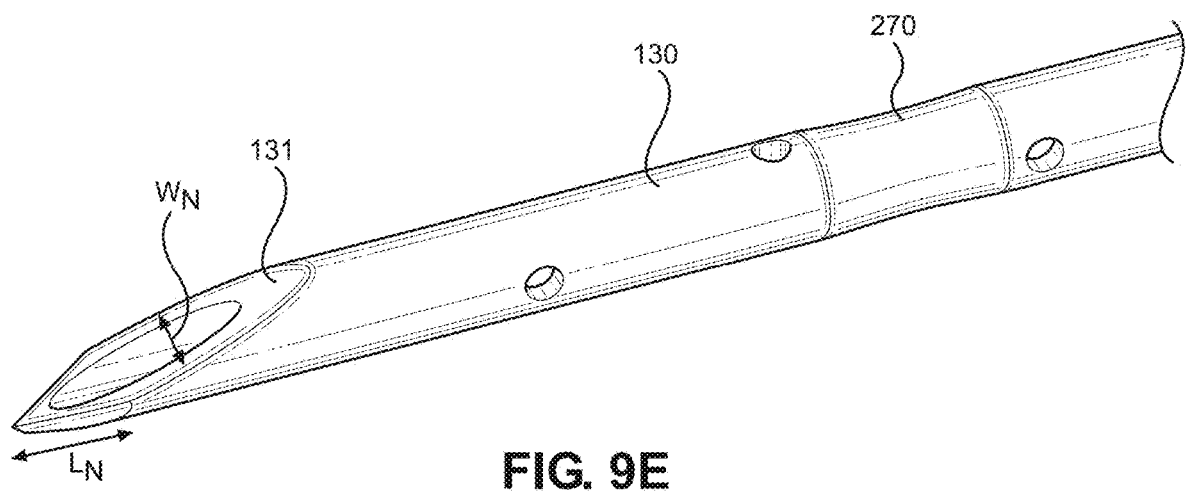
FIG. 9E illustrates a perspective view of an implementation of a sharp needle tip of the needle according to the present disclosure.
Figure 9F:
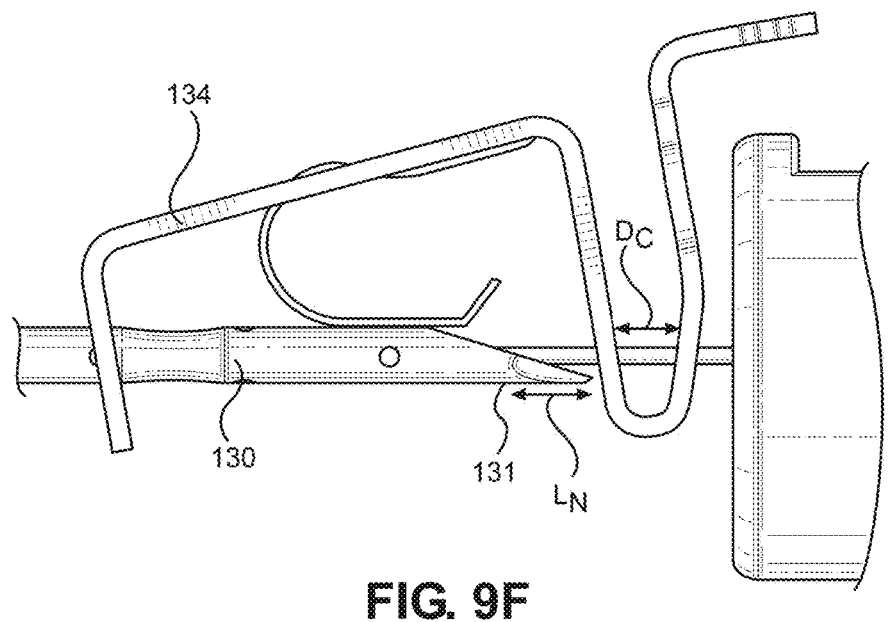
FIG. 9F illustrates the sharp needle tip being withdrawn from the needle safety clip.

Referring to FIG. 9E, a perspective view of the sharp needle tip 131 of the needle cannula 130 is illustrated. The sharp needle tip 131 may be formed by back grinding as illustrated, or in other implementations, the sharp needle tip 131 may have a lancet tip. The sharp needle tip 131 tapers in the distal direction such that the width $W_n$ of the sharp needle tip 131 at a plane along the sharp needle tip 131 is equal to the width of the rectangular bottom region 192. As such, the needle cannula 130 cannot extend distally past the first distal wall 190 beyond that plane where the sharp needle tip 131 has the width $W_n$ when the needle safety clip 134 is released from the rigid hub 120 because the needle cannula 130 is wider than the rectangular bottom region 192 proximal of that plane. However, the length $L_n$ may still extend distally beyond the first distal wall 190 because the needle cannula 130 is thinner than the rectangular bottom region 192 distal of that plane. Therefore, as shown in FIG. 9F, to prevent exposure of the sharp needle tip 131 beyond the second distal wall 194, the needle safety clip 134 is designed so that the distance $D_c$ between the first distal wall 190 and the second distal wall 194 in the axis aligned with the longitudinal axis of the needle cannula 130 is greater than the length $L_n$.

As shown throughout the FIGS. 9A-9F, the needle cannula 130 may further comprise a swage 270 having a pressed area of the metal tube near the distal tip of the needle. The swage may have a substantially oval-shaped, or ellipse-shaped, cross sectional bulge that differs from the round cross section of the rest of the needle. The major diameter of the oval-shaped swage 270 is smaller than the cut out portions of the first and second distal walls 190, 194 of the safety latch 134, but is larger than the hole 182 in the proximal wall 180. This arrangement further ensures the safety clip 134 cannot be pulled distally off the tip of the needle.

Additionally, the minor diameter of the oval-shaped swage is larger than the width of the rectangular bottom region cut out 192 in the first distal wall of the safety latch. This ensures that the safety would not spring upward when the swage passes by the first distal wall 190 even if the rectangular bottom region 192 slot of the safety is parallel to the swage instead of being perpendicular, as it normally is. Moreover, the inner diameter of the swage 270 is greater than the outer diameter of the guidewire 132 so that the guidewire 132 can pass therethrough.

Figure 10A:
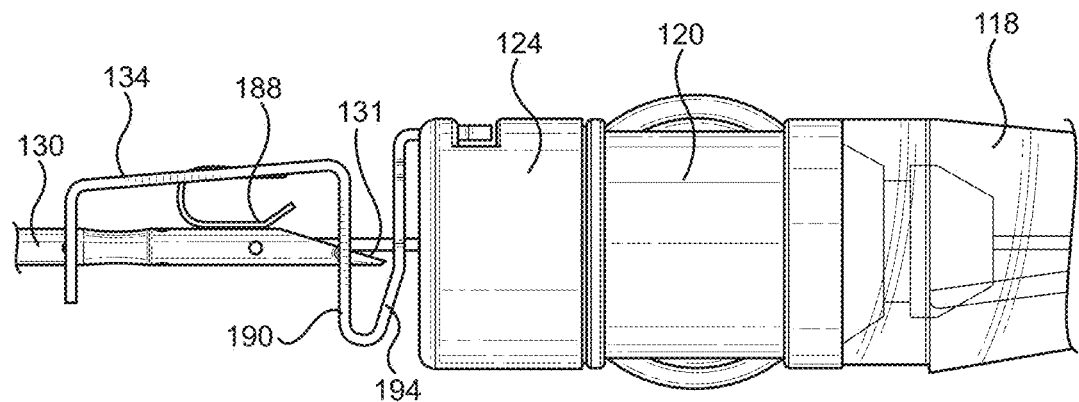
FIG. 10A illustrates the insertion group being pulled proximally to the point where the sharp needle tip of the needle is between two distal walls of the needle safety clip.
Figure 10B:
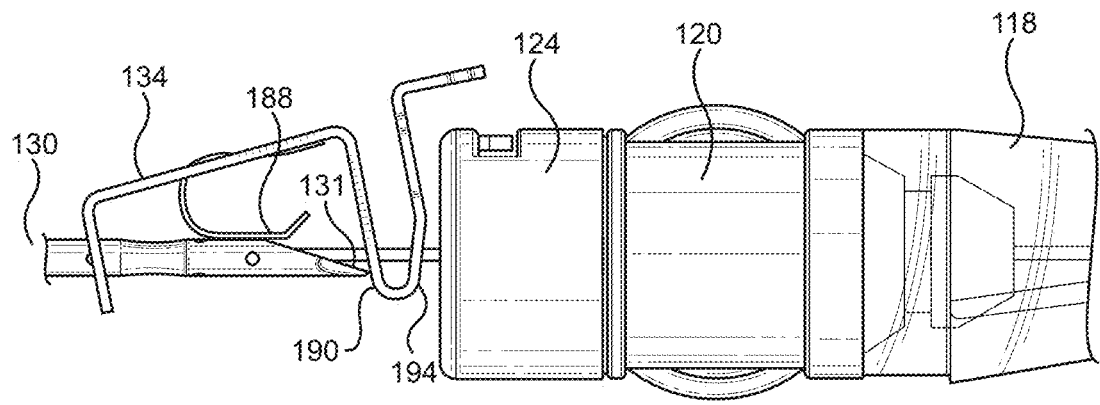
FIG. 10B illustrates the insertion group being pulled proximally to the point where the sharp needle tip of the needle is proximal of both the two distal walls of the needle safety clip and is tilted relative to the needle safety clip.

Referring to FIGS. 10A-B, partially transparent side views of the catheter insertion device 100 during separation of the catheter group 102 are illustrated. As explained above in connection with FIG. 8D, the slider 138 is initially slid proximally to provide clearance to allow the needle support 142 to swing upwards, and then the release 140 is slid distally to push the catheter advancer base 318 forward. The practitioner can then fully advance the catheter into the patient, i.e. until the distal end of the catheter hub 118 almost touches the skin. The practitioner then uses the hand that is not grasping the handle 110 to stabilize the catheter group 102. For example, the practitioner can use his non-dominant hand to grasp the catheter hub 118 and/or the rigid hub 120 to stabilize the rigid hub 120 at a constant position within the vasculature of the patient. The practitioner can then pull the insertion group 104 proximally to remove the needle cannula 130 from the catheter group 102.

As shown in FIG. 10A, the insertion group 104 is pulled proximally to the point where the sharp needle tip 131 of the needle cannula 130 is proximal of the second distal wall 194, but still distal of the first distal wall 190. As such, the plane where the sharp needle tip 131 has the width $W_n$ is still distal of the first distal wall 190 and the needle cannula 130 is stabilized within the round top region 191. As shown in FIG. 10B, the width, $W_n$, of the sharp needle tip 131 is less than the width of the rectangular bottom region 192 and, therefore, the needle safety clip is free to tilt relative to the needle cannula. The spring arm 188 then decompresses to tilt the needle safety clip upward, so that the second distal wall 194 and/or the first distal wall 190 cover the sharp needle tip 131.

Figure 11A:
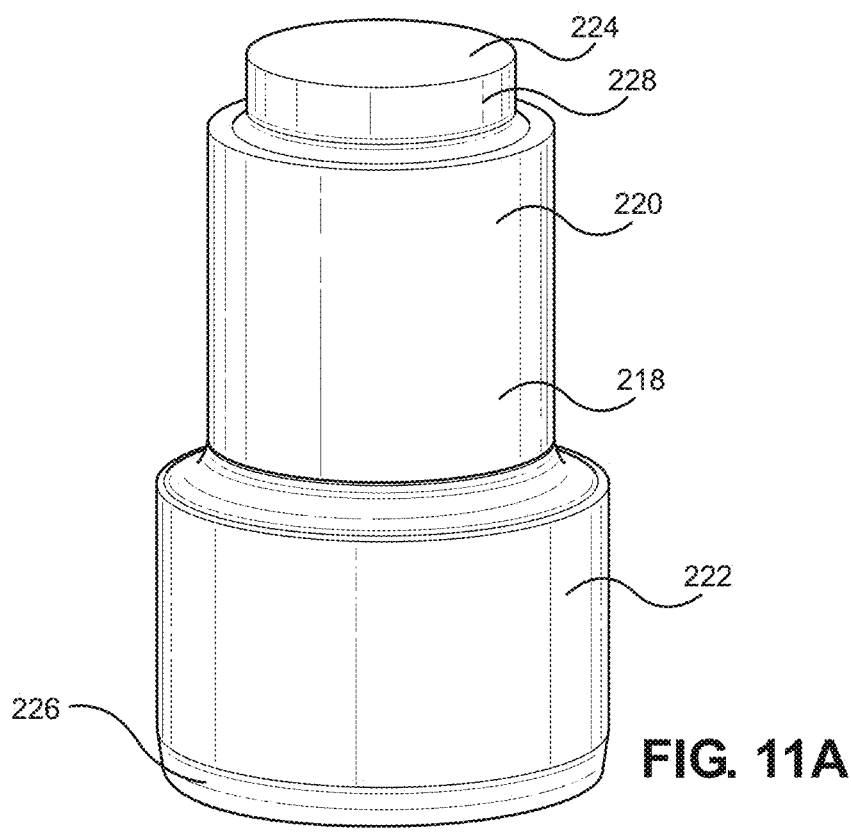
FIG. 11A illustrates a perspective view of an implementation of a seal having two parts according to the present disclosure.
Figure 11B:
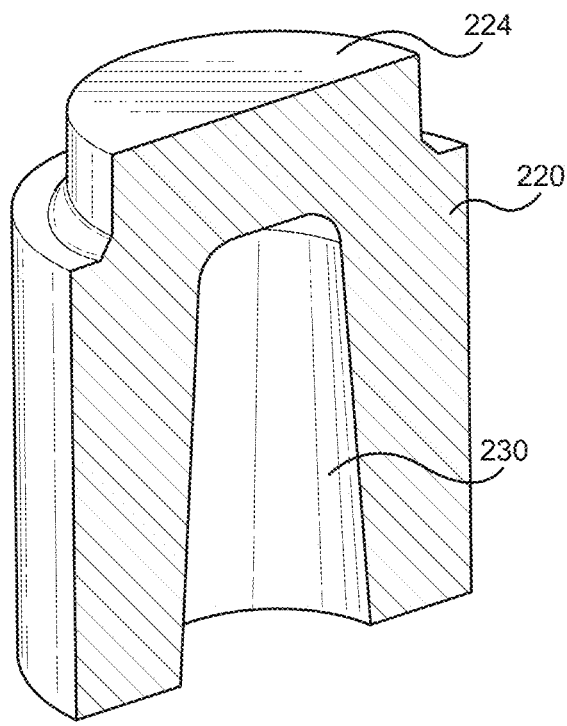
FIG. 11B illustrates a proximal part of the two-part seal of FIG. 11A.

Referring to FIG. 11A, a perspective view of an implementation of the seal 218 is illustrated. The seal 218 is a two-part seal that includes a proximal part 220 and a distal part 222. Referring to FIG. 11B, the proximal part 220 has a flat proximal face 224 and a proximal region 228 having a reduced diameter. The proximal part 220 defines an inner cavity 230 that extends along a majority of the longitudinal axis of the proximal part 220. Relative to the seal 211, the inner cavity 230 reduces the surface area of the seal 218 that the needle cannula 130 contacts, thereby reducing the frictional forces applied during advancement of the catheter group and removal of the needle cannula 130. According to further aspects, lubricant may be added the cavity 230 to further reduce these frictional forces. Additionally, the cavity 230 also provides empty space for the displaced seal material volume to move into when the cannula is inserted into the seal during the shelf life of the device, i.e. prior to removal of the cannula. This prevents a small portion of the seal material from being displaced out the back of the rigid cap of the catheter or distally into the catheter, i.e. inside the rigid catheter hub.

Figure 11C:
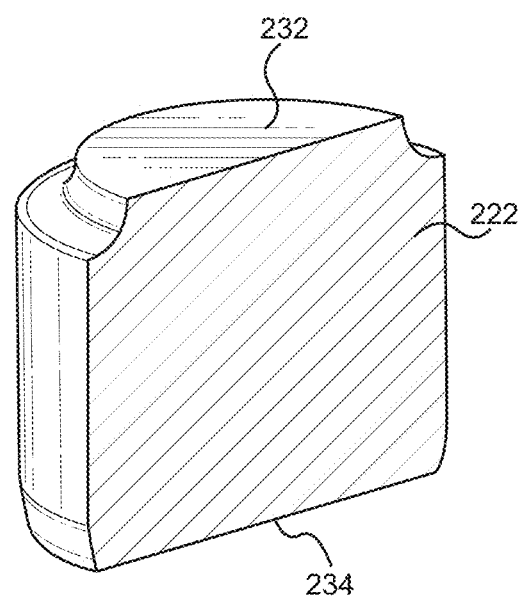
FIG. 11C illustrates a distal part of the two-part seal of FIG. 11A.

Referring to FIG. 11C, the distal part 222 is solid and includes a proximal region 232 of reduced diameter. The diameter of the proximal region 232 is slightly smaller than the diameter of the inner cavity at the distal end of the proximal part 220 to prevent lateral movement of the distal part 222 relative to the proximal part 220 when the seal 218 is assembled within the rigid hub 120 and the rigid hub cap 124. The distal part 222 also has a tapered distal region with a diameter that reduces distally. The seal 218 may be made of a resilient material, such as, for example, silicon, rubber, polyisoprene, or the like.

Figure 11D:
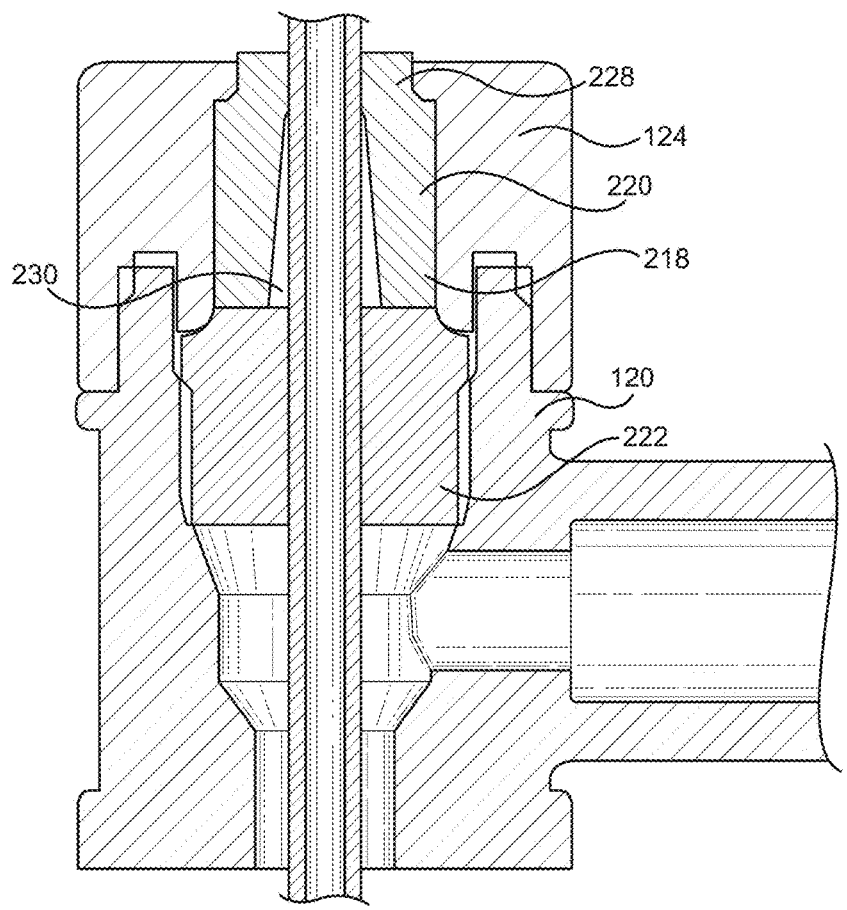
FIG. 11D illustrates a partial cross-sectional view of seal of FIG. 11A within the catheter hub of the catheter group.

Referring to FIG. 11D, a partial cross-sectional view of the assembled rigid hub 120, two-part seal 218, and rigid hub cap 124 taken along the plane defined by the diameter of the rigid hub 120 and the longitudinal axis of the side port 121 is illustrated. The proximal region 228 having the reduced diameter is compressed within the rigid hub cap 124 to force the seal material radially inward in response to pressure applied to the flat distal face 226. The flat distal face 226 is flush with the distal end of the rigid hub cap 124 to allow for complete evacuation of the inner volume of the rigid hub 120 when flushing the catheter insertion device 100.

As shown in FIG. 11D, the distal seal diameter is larger than the diameter of the mating cavity in the rigid hub. This helps to generate a compression force to prevent air or fluid leakage after the needle/cannula is removed during routine use of the catheter by the practitioner, such as for drawing blood or injecting fluid. Further, the radiused portion on the distal seal (in the middle of the assembly) mates with the corresponding radius on the inside of the rigid cap to facilitate placement and location of the distal seal, as well as resist pressure from the distal end inside the catheter body and extension line in order to keep the seal in place. Additional compression forces on the proximal side of the seal further close off the previous hole from the cannula. Also, the proximal side of the seal may be flush, or just beyond flush, with the outside of the rigid cap to allow cleaning of the hub.

Figure 12:
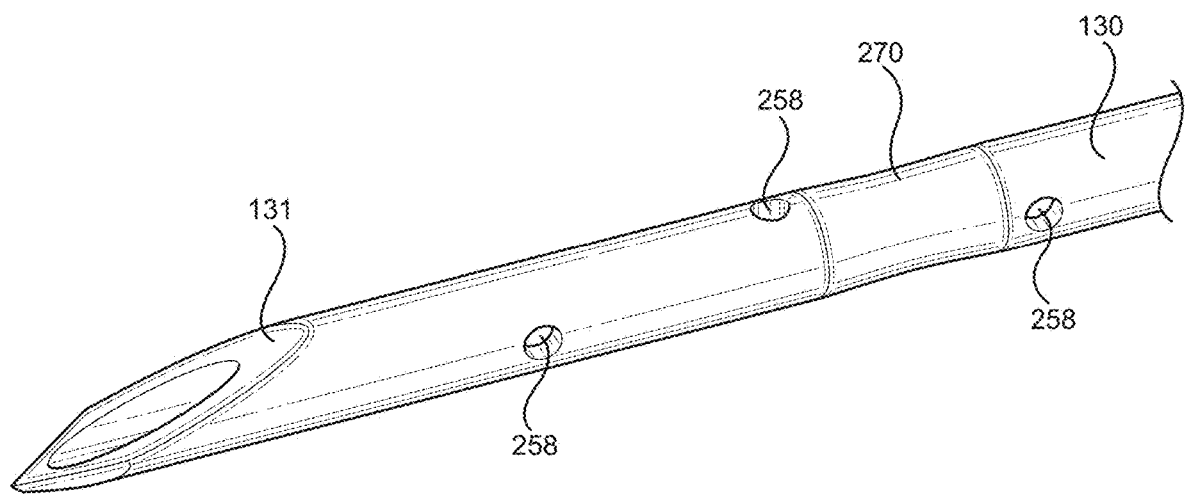
FIG. 12 illustrates a perspective view of a distal region of the needle showing a plurality of echogenic features.

Referring to FIG. 12, a perspective view of a distal region of the needle cannula 130 is illustrated. The distal region of the needle cannula 130 includes one or more and, preferably, eight echogenic features. The echogenic features may be, for example, through holes 258 drilled within opposite sides of the needle cannula 130. Although the sharp needle tip 131 is echogenic when observed under ultrasound, the through holes 258 improve the echogenicity of the needle cannula 130. In particular, the through holes 258 are visible through the wall thickness of the elongated catheter 106 under ultrasound. In addition, through holes 258 allow for blood flow from within the lumen of the needle cannula 130 to the outer surface of the needle cannula 130. The blood then flows to the inner surface of the catheter 106 to allow for visual observation of the blood.

The through holes 258 are angled relative to one another. For example, the through holes 258 are drilled 90 degrees apart from one another, as shown in FIG. 12. The different angles of the through holes 258 and the number of through holes 258 results in at least two echogenic features being visible under ultrasound at all times—one echogenic feature being the sharp needle tip 131 and the other being at least one of the through holes 258. The two visible echogenic features enable the practitioner to know the angle of insertion of the needle cannula 130.

The many features and advantages of the catheter insertion device 100 are apparent from the detailed specification, and thus, the claims cover all such features and advantages within the scope of this application. Further, numerous modifications and variations are possible. As such, it is not desired to limit the catheter insertion device 100 to the exact construction and operation described and illustrated. Accordingly, all suitable modifications and equivalents may fall within the scope of the appended claims.

What is claimed is:

1. A catheter insertion device comprising:
    a handle having a body portion, a top arm extending distally from the body portion, and a bottom arm extending distally from the body portion;
    a needle cannula having a proximal end located within the handle body portion and a sharp distal tip extending distally from the top and bottom arms;
    a catheter assembly removably coupled to the handle and configured to slide on the needle cannula, the catheter assembly having a portion disposed in a space between the top arm and the bottom arm, the catheter assembly comprising an elongated catheter, a catheter hub connected to the elongated catheter, and a catheter advancer base removably connected to the catheter hub, the catheter advancer base slidably disposed between the top arm and the bottom arm, and the catheter advancer base having a grip portion for gripping and advancing the catheter assembly from a first position to a second position;
    a guidewire partially disposed within the handle; and
    a guidewire actuator connected to the handle and to the guidewire, the guidewire actuator configured to slide along the top arm of the handle for extending or retracting the guidewire relative to the handle.

2. The catheter insertion device according to claim 1, wherein the catheter advancer base includes a pair of laterally extending grip arms configured to aid with gripping the catheter assembly by a user.

3. The catheter insertion device according to claim 2, wherein the catheter advancer base further comprises a seat portion configured to secure the catheter and the catheter hub to the catheter advancer base.

4. The catheter insertion device according to claim 3, wherein the seat portion of the catheter advancer base comprises a pair of spaced apart fasteners for securing the catheter advancer base to the catheter hub such that the catheter hub stays connected to and moves with the catheter advancer base when the catheter advancer base is advanced distally during a catheter insertion procedure.

5. The catheter insertion device according to claim 2, wherein the catheter advancer base further comprises a retaining member configured to secure the catheter hub to the catheter advancer base, such that the catheter hub stays connected to and moves with the catheter advancer base when the catheter advancer base is advanced distally during a catheter insertion procedure.

6. The catheter insertion device according to claim 5, wherein a proximal end of the guidewire is connected to the guidewire actuator.

7. The catheter insertion device according to claim 6, wherein the top arm of the handle includes a groove, the guidewire actuator including a portion disposed in the groove to guide the guidewire actuator when the guidewire actuator slides along the top arm of the handle to extend or retract the guidewire relative to the handle.

8. The catheter insertion device according to claim 1, wherein the catheter advancer base is configured to prevent twisting of the catheter assembly during movement of the catheter assembly from the first position to the second position.

9. The catheter insertion device according to claim 8, wherein the catheter advancer base is configured to slide along the bottom arm of the handle.

10. The catheter insertion device according to claim 9, wherein the catheter advancer base includes a guide portion configured to receive the bottom arm of the handle for guiding the catheter assembly from the first position to the second position.

11. The catheter insertion device according to claim 1, further comprising a needle support connected to the handle and movable between a closed position and an open position, the needle support configured to block distal advancement of the catheter assembly when in the closed position, and the needle support further configured to permit distal advancement of the catheter assembly when in the open position.

12. The catheter insertion device according to claim 11, wherein the needle support is further configured to stabilize lateral movement of the needle cannula when the needle support is in the closed position during an insertion procedure.

13. The catheter insertion device according to claim 11, wherein the needle support includes a pair of parallel walls pivotally connected to the handle, said needle support configured to support the needle cannula when the needle support is in the closed position.

14. The catheter insertion device according to claim 13, wherein said needle cannula is disposed between the pair of parallel walls of the needle support when the needle support is in the closed position.

15. The catheter insertion device according to claim 11, wherein the needle support cannot move from the closed position to the open position before the guidewire actuator is moved to extend the guidewire distally relative to the handle.

16. The catheter insertion device according to claim 11, wherein the guidewire actuator abuts the needle support when the needle support is in the closed position, wherein the guidewire actuator does not abut the needle support when the needle support is in the open position.

17. The catheter insertion device according to claim 11, wherein the needle support is pivotally connected to a distal portion of the top arm of the handle and configured to move relative to the handle upon abutment of the catheter advancer base with the needle support.

18. The catheter insertion device according to claim 1, further comprising a catheter assembly actuator connected to the handle, the catheter assembly actuator being movable relative to the handle to slide the catheter assembly distally relative to the handle.

19. The catheter insertion device according to claim 1, wherein the guidewire further has a variable stiffness.

20. The catheter insertion device according to claim 1, wherein the housing further includes a gripping surface to assist a user with single-handed operation of the catheter insertion device.

\* \* \* \* \*